US009950138B2

(12) United States Patent
O'Callaghan et al.

(10) Patent No.: US 9,950,138 B2
(45) Date of Patent: Apr. 24, 2018

(54) INDWELLING URINARY CATHETER

(71) Applicants: UNIVERSITY OF UTAH RESEARCH FOUNDATION, Salt Lake City, UT (US); ADVANCECATH LLC, Cottonwood Heights, UT (US)

(72) Inventors: Ryan James O'Callaghan, Cottonwood Heights, UT (US); Garrett Curtis Coman, Salt Lake City, UT (US); William O. Brant, Salt Lake City, UT (US); Nicholas Ray Blickenstaff, Salt Lake City, UT (US); Christopher Noel Cindrich, Draper, UT (US)

(73) Assignees: University of Utah Research Foundation, Salt Lake City, UT (US); AdvanceCath LLC, Cottonwood Heights, UT (US)

( * ) Notice: Subject to any disclaimer, the term of this patent is extended or adjusted under 35 U.S.C. 154(b) by 373 days.

(21) Appl. No.: 14/416,714

(22) PCT Filed: Jul. 19, 2013

(86) PCT No.: PCT/US2013/051206
§ 371 (c)(1),
(2) Date: Jan. 23, 2015

(87) PCT Pub. No.: WO2014/018386
PCT Pub. Date: Jan. 30, 2014

(65) Prior Publication Data
US 2015/0196730 A1 Jul. 16, 2015

Related U.S. Application Data

(60) Provisional application No. 61/782,361, filed on Mar. 14, 2013, provisional application No. 61/741,561, filed on Jul. 23, 2012.

(51) Int. Cl.
*A61M 25/00* (2006.01)
*A61M 25/04* (2006.01)
(52) U.S. Cl.
CPC ........ *A61M 25/0017* (2013.01); *A61M 25/04* (2013.01); *A61M 2025/0004* (2013.01)
(58) Field of Classification Search
CPC .............. A61M 25/0017; A61M 25/04; A61M 2025/0004; A61M 2210/1089;
(Continued)

(56) References Cited

U.S. PATENT DOCUMENTS 1,661,494 A 3/1928 Nielsen
2,213,210 A 9/1940 Egbert
(Continued)

FOREIGN PATENT DOCUMENTS

WO WO 2014/018386 1/2014

OTHER PUBLICATIONS

International Search Report and Written Opinion for Application No. PCT/US2013/051206 dated Oct. 24, 2013 (12 pages).
(Continued)

*Primary Examiner* — Adam Marcetich
(74) *Attorney, Agent, or Firm* — Michael Best & Friedrich LLP

(57) ABSTRACT

A urinary catheter generally includes a core lumen, a bladder retention mechanism, and a stent. The core lumen is insertable into a urethra, and defines an inlet end and an outlet end opposite the inlet end. The bladder retention mechanism is coupled to the inlet end of the core lumen for hingedly moving between a release position and a retention position. The stent is coaxially mounted on the core lumen adjacent the bladder retention mechanism, and defines a stent inlet (Continued)

configured to receive a fluid from the bladder, and a stent outlet configured to discharge the fluid around the core lumen and into the urethra.

23 Claims, 21 Drawing Sheets

(58) Field of Classification Search
 CPC .. A61M 2210/1092; A61M 2210/1096; A61M 27/008; A61M 2210/1085; A61M 2210/1078; A61M 2025/0079; A61M 25/02; A61M 2025/0293; A61M 2025/0024; A61M 25/0074; A61B 2018/00279; A61B 2017/3484
 See application file for complete search history.

(56) References Cited

U.S. PATENT DOCUMENTS

| | | | |
|---|---|---|---|
| 2,547,758 A | | 4/1951 | Keeling |
| 2,642,874 A | | 6/1953 | Keeling |
| 2,940,450 A | | 6/1960 | Witt et al. |
| 3,108,595 A | | 10/1963 | Overment |
| 3,397,699 A | | 8/1968 | Kohl |
| 3,490,457 A | | 1/1970 | Petersen |
| 3,713,447 A | * | 1/1973 | Adair .................. A61M 25/06 604/105 |
| 3,938,530 A | * | 2/1976 | Santomieri ........... A61M 25/04 604/105 |
| 3,990,447 A | | 11/1976 | Vega |
| 4,222,384 A | | 9/1980 | Birtwell |
| 4,228,802 A | | 10/1980 | Trott |
| 4,276,874 A | * | 7/1981 | Wolvek ............... A61M 1/1072 600/18 |
| 4,337,775 A | | 7/1982 | Cook et al. |
| 4,419,097 A | | 12/1983 | Rowland |
| 4,424,058 A | | 1/1984 | Parsons et al. |
| 4,553,959 A | | 11/1985 | Hickey et al. |
| 4,579,554 A | | 4/1986 | Glassman |
| 4,627,838 A | | 12/1986 | Cross et al. |
| 4,660,560 A | | 4/1987 | Klein |
| 4,810,247 A | | 3/1989 | Glassman |
| 4,878,901 A | | 11/1989 | Sachse |
| 4,957,479 A | | 9/1990 | Roemer |
| 4,995,868 A | | 2/1991 | Brazier |
| 5,007,897 A | | 4/1991 | Kalb et al. |
| 5,073,166 A | * | 12/1991 | Parks .................. A61J 15/0015 604/105 |
| 5,120,316 A | | 6/1992 | Morales et al. |
| 5,232,440 A | | 8/1993 | Wilk |
| 5,255,679 A | | 10/1993 | Imran |
| 5,269,755 A | | 12/1993 | Bodicky |
| 5,269,802 A | | 12/1993 | Garber |
| 5,286,254 A | | 2/1994 | Shapland et al. |
| 5,300,022 A | | 4/1994 | Klapper et al. |
| 5,318,041 A | | 6/1994 | DuBois et al. |
| 5,344,439 A | | 9/1994 | Otten |
| 5,352,198 A | | 10/1994 | Goldenberg et al. |
| 5,419,764 A | | 5/1995 | Roll |
| 5,445,626 A | | 8/1995 | Gigante |
| 5,454,790 A | | 10/1995 | Dubrul et al. |
| 5,458,568 A | | 10/1995 | Racchini et al. |
| 5,520,636 A | | 5/1996 | Korth et al. |
| 5,562,622 A | | 10/1996 | Tihon |
| 5,591,145 A | * | 1/1997 | Sachse ................. A61F 2/04 604/317 |
| 5,637,091 A | | 6/1997 | Hakky et al. |
| 5,681,280 A | | 10/1997 | Rusk et al. |
| 5,738,654 A | | 4/1998 | Tihon |
| 5,749,826 A | | 5/1998 | Faulkner |
| 5,865,815 A | | 2/1999 | Tihon |
| 5,980,507 A | | 11/1999 | Fassuliotis et al. |
| 6,017,323 A | | 1/2000 | Chee |
| 6,052,612 A | | 4/2000 | Desai |
| 6,053,897 A | | 4/2000 | Sachse |
| 6,080,142 A | | 6/2000 | Sachse |
| 6,494,855 B2 | | 12/2002 | Rioux et al. |
| 6,527,737 B2 | | 3/2003 | Kaneshige |
| 6,547,761 B2 | | 4/2003 | Liu |
| 6,558,350 B1 | | 5/2003 | Hart et al. |
| 6,589,208 B2 | | 7/2003 | Ewers et al. |
| 6,673,060 B1 | | 1/2004 | Fleming, III |
| 6,837,871 B2 | | 1/2005 | Gonzales et al. |
| 6,855,126 B2 | | 2/2005 | Flinchbaugh |
| 6,942,641 B2 | | 9/2005 | Seddon |
| 7,141,038 B2 | | 11/2006 | Whalen et al. |
| 7,347,866 B2 | | 3/2008 | Daignault et al. |
| 7,438,711 B2 | | 10/2008 | Deniega et al. |
| 7,527,651 B2 | | 5/2009 | Gellman |
| 7,662,145 B2 | | 2/2010 | Bolmsjö et al. |
| 7,753,906 B2 | | 7/2010 | Esposito |
| 7,758,542 B2 | | 7/2010 | Whalen et al. |
| 7,766,899 B2 | | 8/2010 | Bolmsjö et al. |
| 7,951,064 B2 | | 5/2011 | Whalen et al. |
| 7,959,611 B2 | | 6/2011 | Harvey et al. |
| 8,007,458 B2 | | 8/2011 | Lennox et al. |
| 8,137,309 B2 | | 3/2012 | Nishtala et al. |
| 8,137,337 B2 | | 3/2012 | Hakky et al. |
| 8,177,741 B2 | | 5/2012 | Hammack et al. |
| 2002/0072788 A1 | * | 6/2002 | Hammond ............ A61F 2/0009 623/1.11 |
| 2002/0143292 A1 | * | 10/2002 | Flinchbaugh ......... A61F 5/4405 604/107 |
| 2004/0044307 A1 | | 3/2004 | Richardson et al. |
| 2004/0181235 A1 | * | 9/2004 | Daignault ............. A61M 25/04 606/108 |
| 2004/0193283 A1 | | 9/2004 | Rioux et al. |
| 2004/0243104 A1 | * | 12/2004 | Seddon ................. A61M 25/04 604/540 |
| 2005/0070951 A1 | * | 3/2005 | Paganon ........... A61B 17/22031 606/198 |
| 2007/0276415 A1 | * | 11/2007 | Kladakis ............ A61B 17/0057 606/151 |
| 2008/0071250 A1 | | 3/2008 | Crisp |
| 2008/0133025 A1 | | 6/2008 | Daignault et al. |
| 2008/0281291 A1 | | 11/2008 | Tihon et al. |
| 2009/0156977 A1 | * | 6/2009 | Daignault ................. A61F 2/04 604/8 |
| 2009/0157053 A1 | | 6/2009 | Davis et al. |
| 2010/0152862 A1 | | 6/2010 | Rioux et al. |
| 2010/0241219 A1 | | 9/2010 | Willard et al. |
| 2010/0331825 A1 | | 12/2010 | Hakky et al. |
| 2015/0196730 A1 | | 7/2015 | O'Callaghan et al. |

OTHER PUBLICATIONS

Extended European Search Report for Application No. 13822806.9 dated Mar. 17, 2016 (7 pages).
Gould, Centers for Disease Control and Prevention. (2012). "Catheter-Associated Urinary Tract Infection (CAUTI) Toolkit." Retrieved May 4, 2012, from www.cdc.gov/HAI/ca_uti.html, (1-32).
Gould, C, Umscheid, C, Agarwal, R, et al. "Guideline for the Prevention of Catheter-Associated Urinary Tract Infections 2009," Center for Disease Control and Prevention, Atlanta 2009. pp. 1-67.
Kalorama Information. "The Worldwide Market for Catheters." Marketresearch.com, Feb. 2008.
Klevens RM, Edward JR, et al. "Estimating health care-associated infections and deaths in U.S. hospitals, 2002." Public Health Reports 2007; 122:160-166.
Leuck AM, Wright D, Ellingson LA, et al. "Complications of Foley Catheters—Is Infection the Greatest Risk?" The Journal of Urology 2012; vol. 187, 1662-1666, May 2012.
Maki DG, Tambyah PA. "Engineering Out the Risk for Infection with Urinary Catheters." Emerging Infectious Diseases 2001; vol. 7, No. 2, March-April 342-347.
Saint S, Kaufman SR, Rogers MA, et al. "Condom versus indwelling urinary catheters: a randomized trial." J Am Geriatr Soc. 2006; 54(7):1055-1061.

(56) References Cited

OTHER PUBLICATIONS

Saint S, Lipsky BA, Baker PD, et al. "Urinary catheters: what type do men and their nurses prefer?" J Am Geriatr Soc. 1999; 47(12):1453 (1-5).
Tambyah PA, Halvorson KT, Maki DG. "A Prospective Study of Pathogenesis of Catheter-Associated Urinary Tract Infections," 1999; vol. 74, 131-136; Mayo Clin Proc, Feb. 1999.
Warren JW, Platt R, Thomas RJ. "Antibiotic Irrigation and Catheter-Associated Urinary-Tract Infections." N Engl J Med 1978; 299:570-573.

* cited by examiner

INDWELLING URINARY CATHETER

CROSS-REFERENCE TO RELATED APPLICATIONS

This application is a national stage filing under 35 U.S.C. 371 of International Application No. PCT/US2013/051206, filed Jul. 19, 2013, which claims the priority benefit of U.S. Provisional Patent Application No. 61/782,361, filed Mar. 14, 2013, and U.S. Provisional Patent Application No. 61/741,561, filed Jul. 23, 2012, all of which are incorporated herein by reference in their entireties.

BACKGROUND

Catheter-associated urinary tract infection (UTI) is one of the most common hospital-acquired infections (HAI) and has affected 450,000 patients and added approximately $450 million to annual healthcare costs in the US in 2002 (as adjusted to 2007 value). An estimated 13,000 of the patients die from their UTI each year. Foley catheters are the standard of care for patients requiring indwelling catheterization; however, just having an indwelling Foley catheter for over six days may increase the likelihood of developing a UTI from approximately 5 times to approximately 7 times. Two thirds of UTIs from urinary catheters potentially develop when bacteria, usually from the digestive tract, stick to the external surface of the Foley catheter, where there is no flow of urine, presenting a warm, moist, stagnant space that is ideal for biofilm growth. In addition to a risk of infection, Foley catheters can be painful due to their large diameter and may put patient safety at risk due to the large balloon that holds the device in the bladder. Patients who are demented or coming off of anesthesia may attempt to pull their catheter out, which can damage the urethra and potentially require additional surgery to repair, leading to additional costs and the potential for future health problems.

In 2008, the Centers for Medicare and Medicaid Services (CMS) announced that hospital-acquired UTI would no longer be covered, meaning hospitals are responsible for the cost and must focus on prevention rather than treatment of UTI. Additionally, in 2014, the 25% of hospitals with the highest rate of HAI will be subject to a 1% Medicare reimbursement penalty, estimated to be approximately $208 k per hospital. UTI rates are currently published on medicare.gov for around 70% of hospitals and 96% of nursing homes, and will be mandatory effective in 2014. Thus, there has developed a need to decrease infection rates in patients with indwelling urinary catheters.

SUMMARY

In one embodiment, the invention provides a urinary catheter generally including a core lumen, a bladder retention mechanism, and a stent. The core lumen is insertable into a urethra, and defines an inlet end and an outlet end opposite the inlet end. The bladder retention mechanism is coupled to the inlet end of the core lumen for hingedly moving between a release position and a retention position. The stent is coaxially mounted on the core lumen adjacent the bladder retention mechanism, and defines a stent inlet configured to receive a fluid from a bladder, and a stent outlet configured to discharge the fluid around the core lumen and into the urethra.

In another embodiment, the invention provides a method for catheterization generally including advancing a core lumen through a urethra of a patient into a bladder. The core lumen defines an inlet end and an outlet end opposite the inlet end. A bladder retention mechanism is coupled to the inlet end in a release position. A stent is coaxially mounted on the core lumen adjacent the bladder retention mechanism. The stent defines a stent inlet configured to receive a fluid from the bladder, and a stent outlet configured to discharge the fluid stream around the core lumen and into the urethra. The core lumen is moved in a direction from the inlet end toward the outlet end, whereupon the bladder retention mechanism hingedly moves from the release position to a retention position.

In still another embodiment, the invention provides a urinary catheter. The urinary catheter includes a core lumen insertable into a urethra, the core lumen defining an inlet end and an outlet end opposite the inlet end, the inlet end of the core lumen being attached to a plug; a bladder retention mechanism for hingedly moving between a release position and a retention position, the bladder retention mechanism having a socket formed therein into which the plug is fitted; and a stent coaxially mounted on the core lumen adjacent the bladder retention mechanism, the stent defining a stent inlet configured to receive a fluid from a bladder, and a stent outlet configured to discharge the fluid around the core lumen and into the urethra, wherein a pulling force applied to the core lumen removes the plug from the socket such that the bladder retention mechanism is in the release position.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
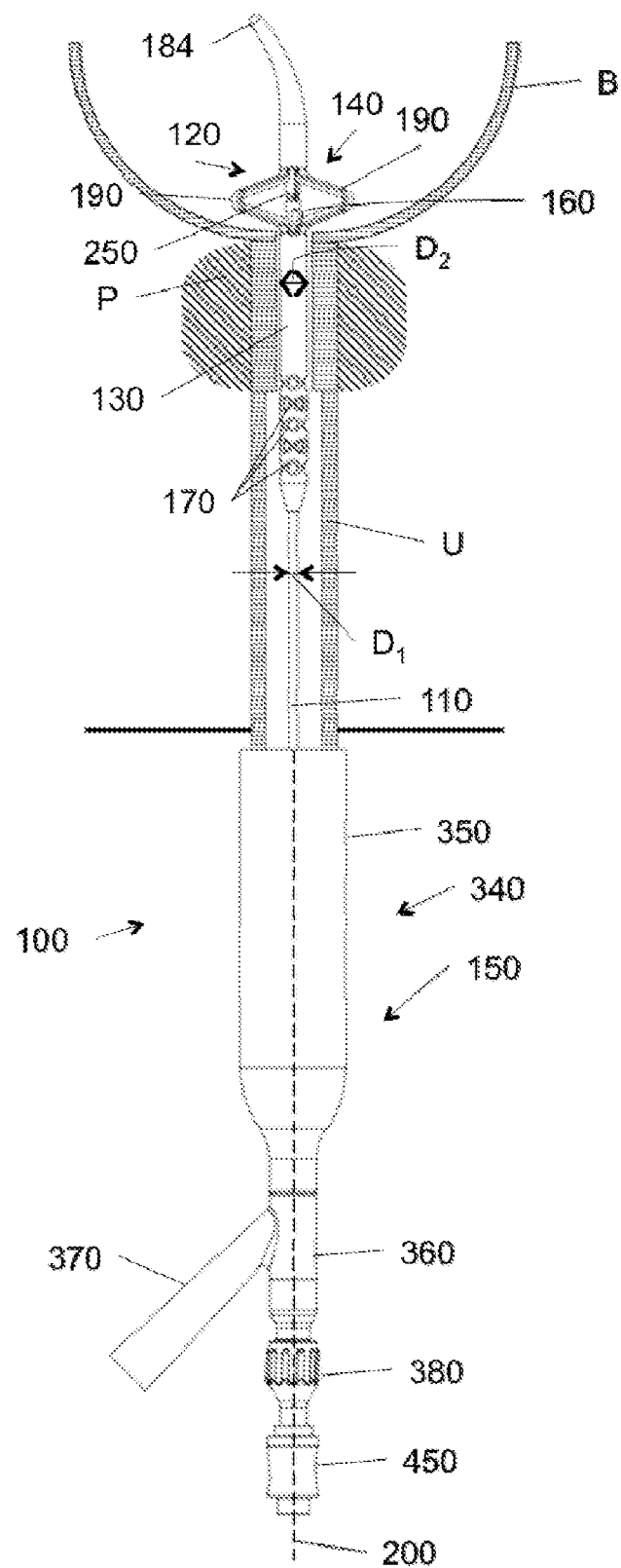
FIG. 1 is a side view of a urinary catheter according to an embodiment of the invention, including a core lumen, a bladder retention mechanism, a stent, and an outlet sheath.
Figure 2:
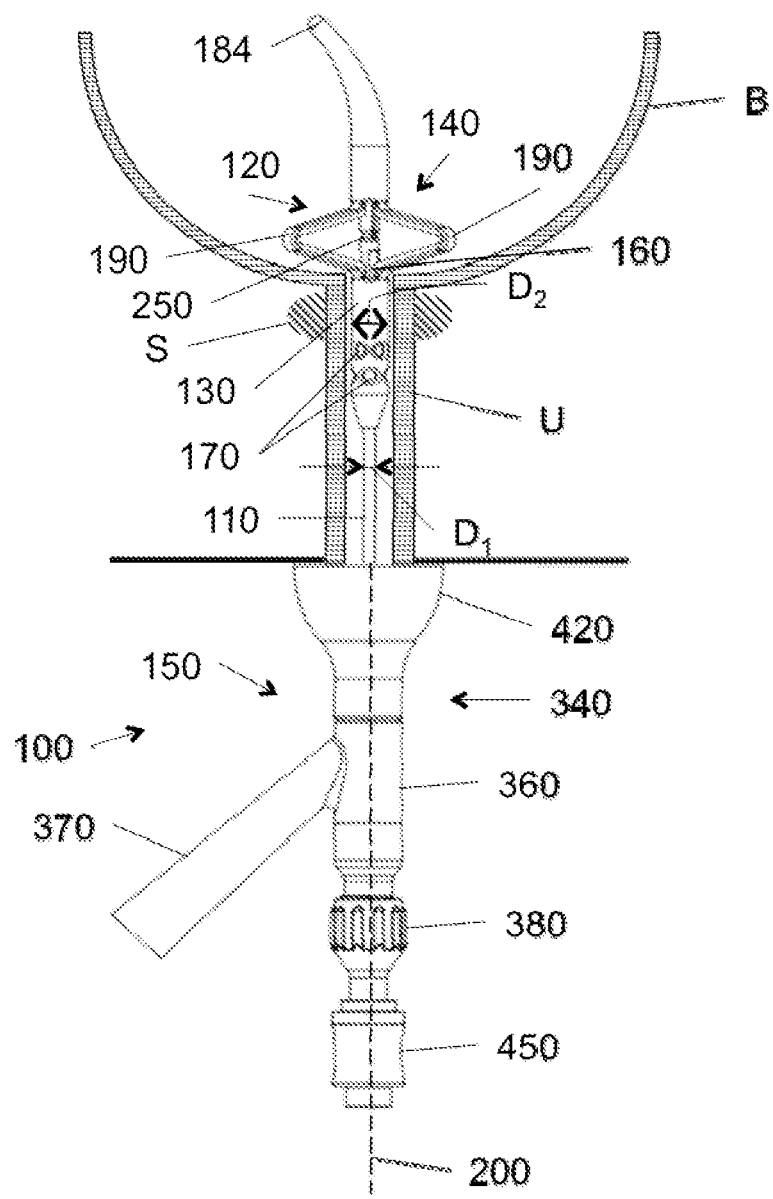
FIG. 2 is a side view of a urinary catheter according to another embodiment of the invention.

Referring to FIG. 1, a urinary catheter 100 includes a core lumen 110, a bladder retention mechanism 120, and a stent 130. The core lumen 110 is insertable into a urethra U, and defines an inlet end 140 and an outlet end 150 opposite the inlet end 140. The bladder retention mechanism 120 is coupled to the inlet end 140 of the core lumen 110 for hingedly moving between a release position (see FIGS. 3-5) and a retention position (see FIGS. 1,2, and 6-9). The stent 130 is coaxially mounted on the core lumen 110 adjacent the bladder retention mechanism 120, and defines a stent inlet 160 configured to receive a fluid (e.g., urine or a urinary stream containing urine plus one or more other fluid) from a bladder B, and a stent outlet 170 configured to discharge the fluid around the core lumen 110 and into the urethra U. In the illustrated embodiment, the stent 130 is positioned adjacent a prostate P, and therefore is a prostatic stent. In other embodiments, other prostheses or structures performing the same function as the prostatic stent 130 disclosed herein can be used instead. In particular, embodiments of the urinary catheter 100 may be adapted for use with a female anatomy, which includes among other changes a female counterpart (e.g., urethral sphincter stent) to the prostatic stent (see FIG. 2). The urinary catheter 100 according to this invention may be made of any physiologically-compatible material having sufficient pliability and elasticity. Such materials are known in the art and include, for example plastics such as polyurethane.

In the illustrated embodiment, the core lumen 110 defines a first outermost diameter $D_1$, and the stent 130 defines a second outermost diameter $D_2$. The second outermost diameter $D_2$ is greater than the first outermost diameter $D_1$. The different outermost diameters $D_1$, $D_2$ can facilitate discharging the fluid around the core lumen 110 and into the urethra U, and also improve patient comfort. In some embodiments, the second outermost diameter $D_2$ is at least two times, at least three times, at least four times, at least five times, or at least ten times the first outermost diameter $D_1$. In other embodiments, the second outermost diameter $D_2$ can be of another ratio to the first outermost diameter $D_1$.

In some embodiments, the first outermost diameter D1 is in a range of about 1.5 mm to about 2.5 mm, and the second outermost diameter $D_2$ is in a range of about 5 mm to about 10 mm. This includes the first outermost diameter $D_1$ of at least 1.5 mm, at least 1.6 mm, at least 1.7 mm, at least 1.8 mm, at least 1.9 mm, at least 2.0 mm, at least 2.1 mm, at least 2.2 mm, at least 2.3 mm, or at least 2.4 mm. In further embodiments, the first outermost diameter $D_1$ is no more than 2.5 mm, no more than 2.4 mm, no more than 2.3 mm, no more than 2.2 mm, no more than 2.1 mm, no more than 2.0 mm, no more than 1.9 mm, no more than 1.8 mm, no more than 1.7 mm, or no more than 1.6 mm. In other embodiments, the first outermost diameter $D_1$ may be of other dimensions.

In some embodiments, the second outermost diameter $D_2$ is at least 5.0 mm, at least 5.1 mm, at least 5.2 mm, at least 5.3 mm, at least 5.4 mm, at least 5.5 mm, at least 5.6 mm, at least 5.7 mm, at least 5.8 mm, at least 5.9 mm, at least 6.0 mm, at least 6.1 mm, at least 6.2 mm, at least 6.3 mm, at least 6.4 mm, at least 6.5 mm, at least 6.6 mm, at least 6.7 mm, at least 6.8 mm, at least 6.9 mm, at least 7.0 mm, at least 7.1 mm, at least 7.2 mm, at least 7.3 mm, at least 7.4 mm, at least 7.5 mm, at least 7.6 mm, at least 7.7 mm, at least 7.8 mm, at least 7.9 mm, at least 8.0 mm, at least 8.1 mm, at least 8.2 mm, at least 8.3 mm, at least 8.4 mm, at least 8.5 mm, at least 8.6 mm, at least 8.7 mm, at least 8.8 mm, at least 8.9 mm, at least 9.0 mm, at least 9.1 mm, at least 9.2 mm, at least 9.3 mm, at least 9.4 mm, at least 9.5 mm, at least 9.6 mm, at least 9.7 mm, at least 9.8 mm, or at least 9.9 mm. In further embodiments, the second outermost diameter $D_2$ is no more than 10.0 mm, no more than 9.9 mm, no more than 9.8 mm, no more than 9.7 mm, no more than 9.6 mm, no more than 9.5 mm, no more than 9.4 mm, no more than 9.3 mm, no more than 9.2 mm, no more than 9.1 mm, no more than 9.0 mm, no more than 8.9 mm, no more than 8.8 mm, no more than 8.7 mm, no more than 8.6 mm, no more than 8.5 mm, no more than 8.4 mm, no more than 8.3 mm, no more than 8.2 mm, no more than 8.1 mm, no more than 8.0 mm, no more than 7.9 mm, no more than 7.8 mm, no more than 7.7 mm, no more than 7.6 mm, no more than 7.5 mm, no more than 7.4 mm, no more than 7.3 mm, no more than 7.2 mm, no more than 7.1 mm, no more than 7.0 mm, no more than 6.9 mm, no more than 6.8 mm, no more than 6.7 mm, no more than 6.6 mm, no more than 6.5 mm, no more than 6.4 mm, no more than 6.3 mm, no more than 6.2 mm, no more than 6.1 mm, no more than 6.0 mm, no more than 5.9 mm, no more than 5.8 mm, no more than 5.7 mm, no more than 5.6 mm, no more than 5.5 mm, no more than 5.4 mm, no more than 5.3 mm, no more than 5.2 mm, or no more than 5.1 mm. In other embodiments, the second outermost diameter $D_2$ may be of other dimensions.

In some embodiments, the first and second diameters $D_1$, $D_2$ may be required to have a particular tolerance dependent on the application. For example, one application may require a tolerance of approximately ±0.01 mm, while another application may allow a tolerance of approximately ±0.1 mm. In some embodiments, one or both of the core lumen 110 and stent 130 may have a cross-sectional shape other than circular (e.g. oval, square, rectangular, or other regular or irregular shapes) in which cases the outermost diameters as used herein may include dimensions other than a diameter, for example the lengths of major axes or the cross-sectional area of the core lumen 110 and stent 130.

In some embodiments, the stent 130 extends along a length that is less than the entire length of the urethra U. For example, the stent 130 may extend along a length from approximately 5 cm to approximately 10 cm. The length of the stent 130 can facilitate discharging urine through the urethra U, thereby flushing out bacteria that may otherwise cause an infection. For example, a urinary catheter that does not provide a continual flow of urine on its external surface may present a warm, moist, and stagnant space that can be ideal for biofilm growth. In contrast, the stent 130 extends along a length that is less than the entire length of the urethra U, thereby allowing urine to flow externally to the core lumen 110 and substantially eliminating the stagnant space.

In this regard, the shortened length of the stent 130 facilitates the use of the body's natural mechanism of flushing the urethral wall to prevent biofilm formation.

Figure 3:
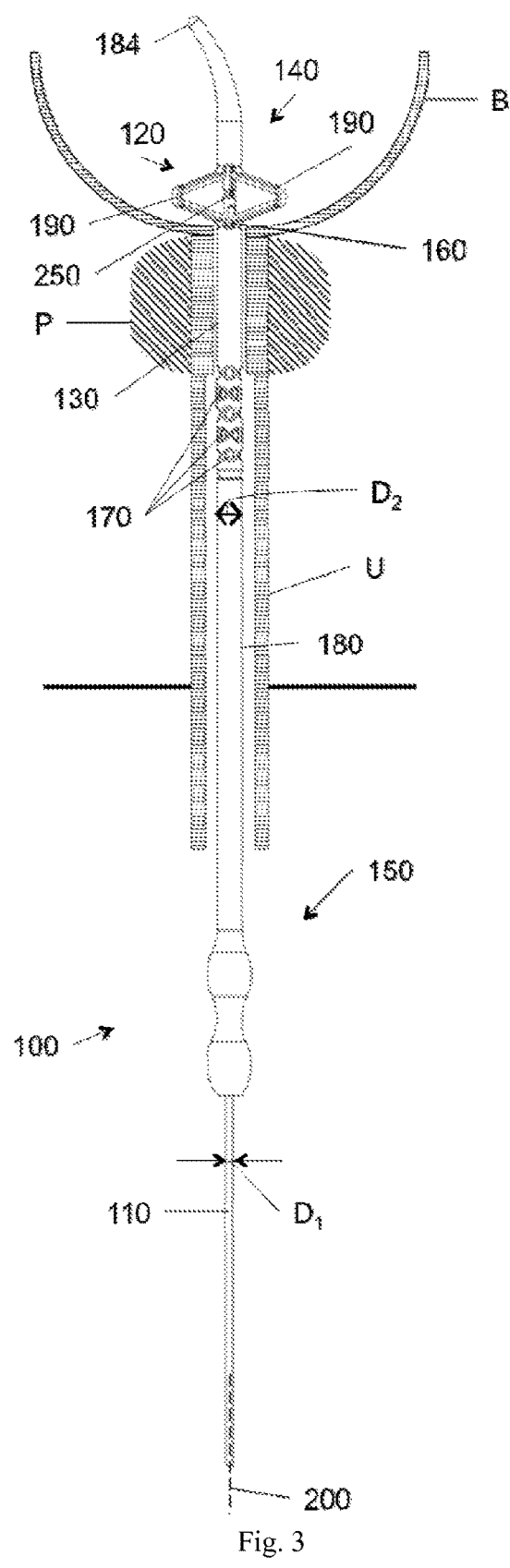
FIG. 3 is an enlarged partial side view of the catheter of FIG. 1.

Referring also to FIG. 3, a stent sheath 180 is slidably coupled to the stent 130. In some embodiments, the stent sheath 180 is dimensioned to matingly receive the stent 130. The stent sheath 180 can facilitate placing the urinary catheter 100. To place the urinary catheter 100, a distal end 184 of the urinary catheter 100 (e.g., a Coude tip) is inserted into the meatus (not shown) with the stent sheath 180 coupled to the stent 130. The distal end 184 is pushed through the urethra U until it reaches the bladder B, which is signaled by urine flowing through the urinary catheter 100. Once the urine has drained, the core lumen 110 is pulled from the outlet end 150 while holding an outside of the stent sheath 180. As explained below, this will activate the bladder retention mechanism 120. A marking on the core lumen 110 may indicate that the core lumen 110 has been pulled far enough in relation to the stent sheath 180 to move the bladder retention mechanism 120 from the release position to the retention position. The stent sheath 180 is then pulled or slid outwardly (i.e., downwardly in FIG. 3) and removed from the urethra U.

Figure 4:
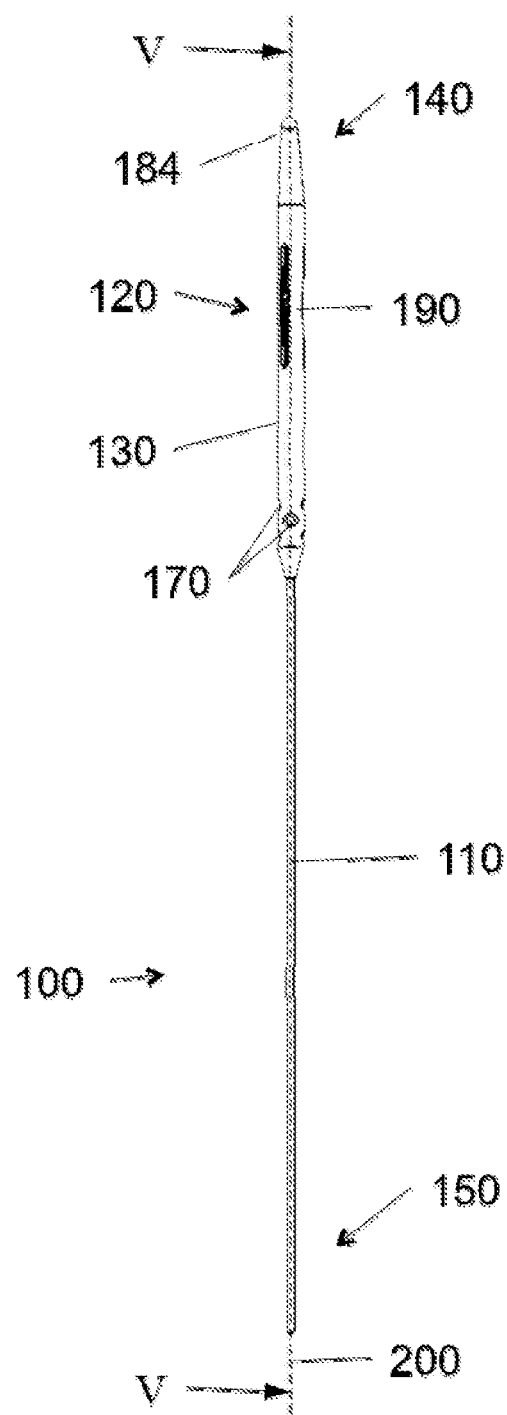
FIG. 4 is side view similar to FIG. 1, illustrating the bladder retention mechanism in a release position.
Figure 5:
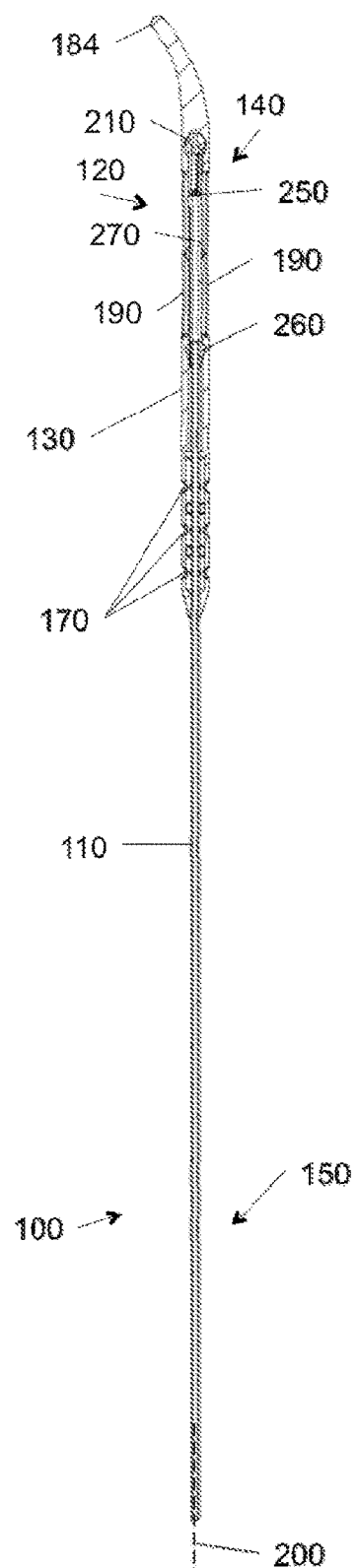
FIG. 5 is a sectional view taken along line V-V of FIG. 4.
Figure 6:
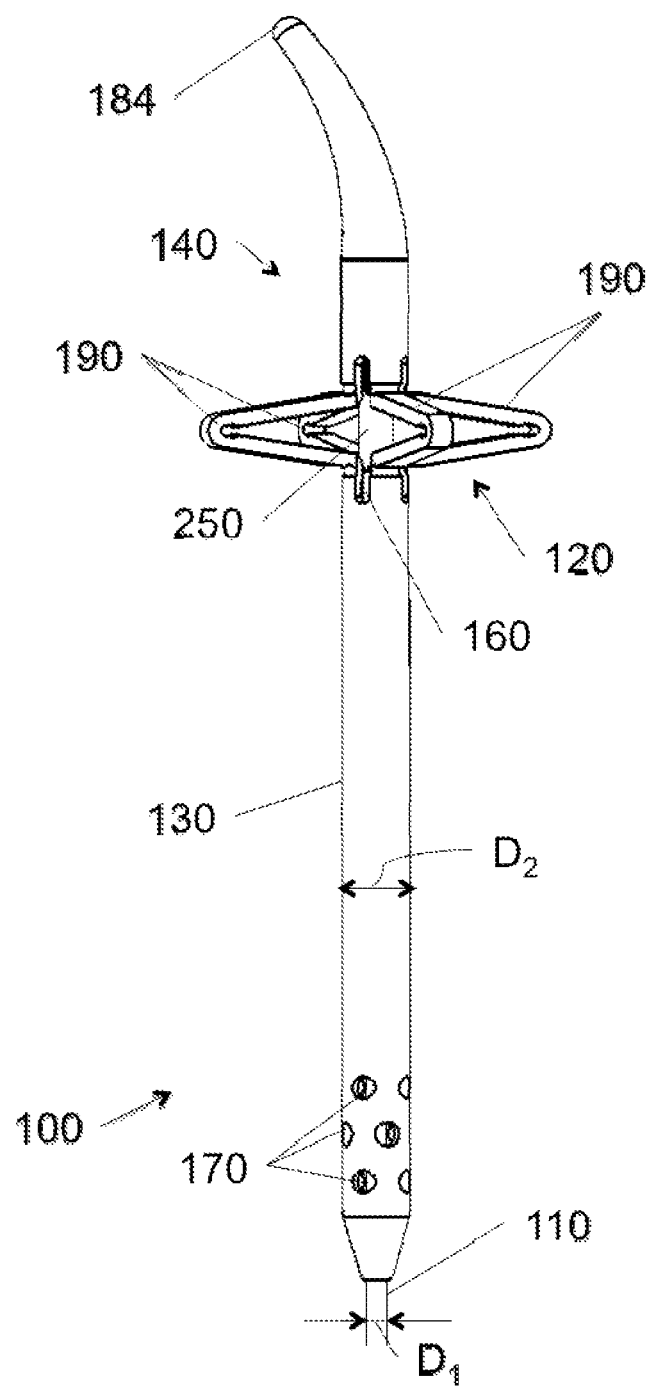
FIG. 6 is an enlarged partial perspective view illustrating the bladder retention mechanism in a retention position.

In the illustrated embodiment, the bladder retention mechanism 120 uses a Malecot type locking mechanism. The bladder retention mechanism 120 includes four pairs of legs or wings 190, which may be extending substantially straight when unencumbered, due to material properties and/or the method of manufacturing. Therefore, in some embodiments, the bladder retention mechanism 120 is configured to resiliently return to a substantially straight, closed, or release position. In other embodiments, the bladder retention mechanism 120 may be formed in other configurations. The illustrated core lumen 110 defines a longitudinal axis 200, and if the bladder retention mechanism 120 is divided into successive imaginary quadrants about the longitudinal axis 200, each quadrant has a respective pair of legs 190. Referring to FIG. 1, only two pairs of legs 190 are shown on the bladder retention mechanism 120; the remaining two pairs of legs 190 would be extending into and out of the plane. Although the illustrated bladder retention mechanism 120 has four pairs of legs or wings 190, one or more legs 190 can be provided, if desired. As illustrated in FIGS. 4 and 5, the legs 190 extend substantially parallel to and adjacent the longitudinal axis 200 when the bladder retention mechanism 120 is in the release position.

Referring also to FIG. 5, the inlet end 140 of the core lumen 110 is coupled to a plug 210. The bladder retention mechanism 120 includes a socket or pocket 220 formed therein. The socket 220 has first and second inner surfaces 230, 240. The first inner surface 230 is closer to the outlet end 150 of the core lumen 110 than the second inner surface 240. The plug 210 is insertable into the socket 220, and abuts the second inner surface 240 when the bladder retention mechanism 120 is in the release position.

In the illustrated embodiment, a projection 250 extends from the plug 210 toward the outlet end 150 of the core lumen 110. The projection 250 includes a tip or head portion 260 that has a larger cross section relative to an adjacent body portion 270. The tip portion 260 of the projection 250 resembles an arrowhead in cross section, pointing toward the outlet end 150 of the core lumen 110 (i.e., downwardly in FIG. 5). That is, the cross section of the tip portion 260 of the projection 250 tapers gradually in thickness in a direction along the longitudinal axis 200 toward the outlet end 150 of the core lumen 110. The stent 130 defines an inner surface with a reduced-diameter portion 280, and the tip portion 260 of the projection 250 is matingly receivable into the reduced-diameter portion 280 when the bladder retention mechanism 120 is in the release position. That is, when the bladder retention mechanism 120 is in the release position, the tip portion 260 of the projection 250 rests on the reduced-diameter portion 280, and is prevented from further moving toward the outlet end 150 of the core lumen 110. Other configurations are possible depending on the usage requirements or preferences for the particular urinary catheter 100, including configurations where the tip portion 260 of the projection 250 has a substantially uniform thickness in cross section.

FIGS. 6-9 illustrate the urinary catheter 100 including the bladder retention mechanism 120 in the retention position. In this position, the legs 190 of the bladder retention mechanism 120 extend away or offset from the longitudinal axis 200. In some embodiments, at least some of the legs 190 extend substantially perpendicular to the longitudinal axis 200 when the bladder retention mechanism 120 is in the retention position. In other embodiments, the legs 190 can extend at a non-zero angle from the longitudinal axis 200 when the bladder retention mechanism 120 is in the retention position. Each leg 190 of the bladder retention mechanism 120 defines a retention area in contact with the bladder B, and moving the bladder retention mechanism 120 toward the retention position increases the retention area, as explained below.

Figure 7:
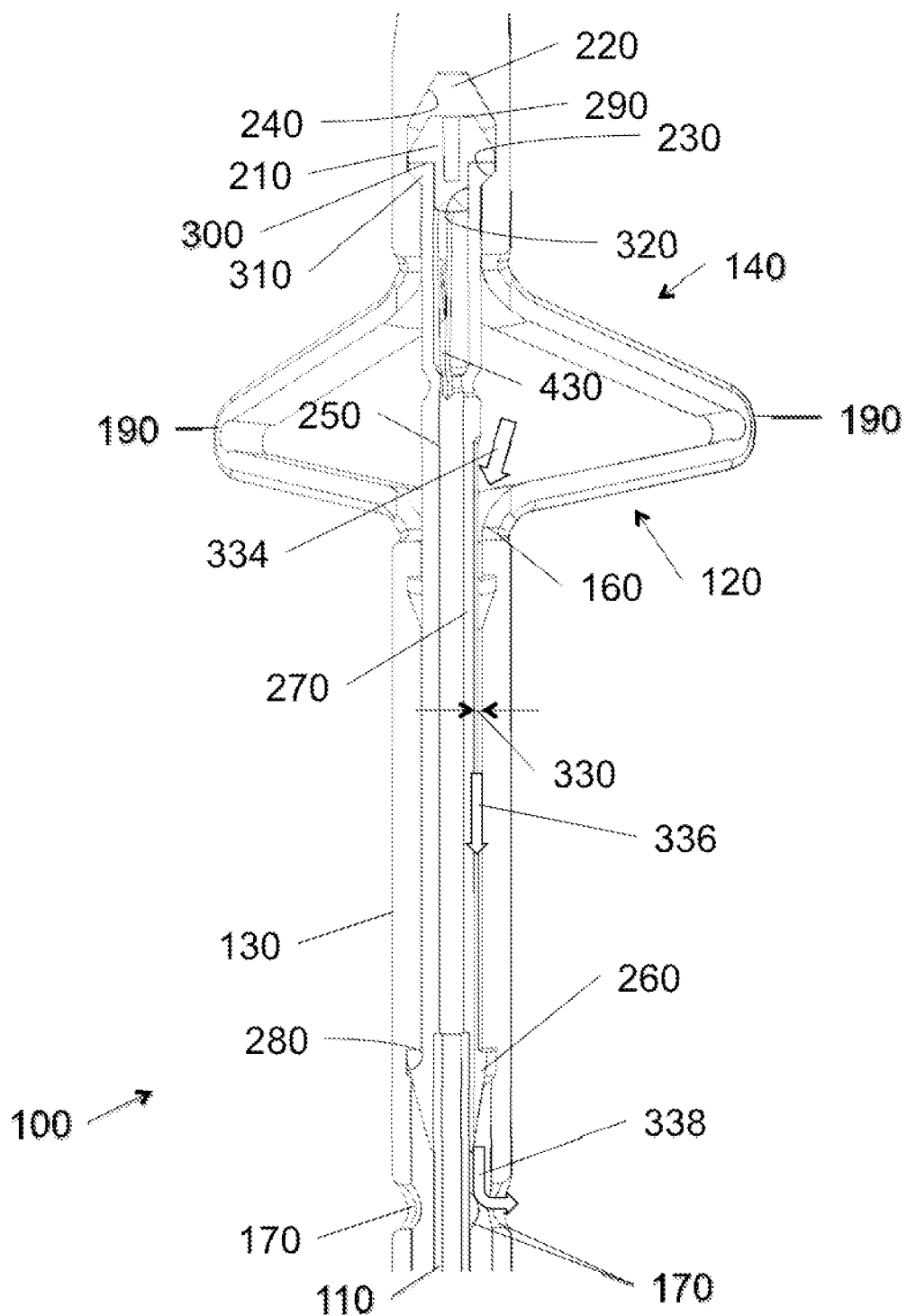
FIG. 7 is an enlarged partial cutaway view of the core lumen, bladder retention mechanism, and stent of FIG. 1.
Figure 8:
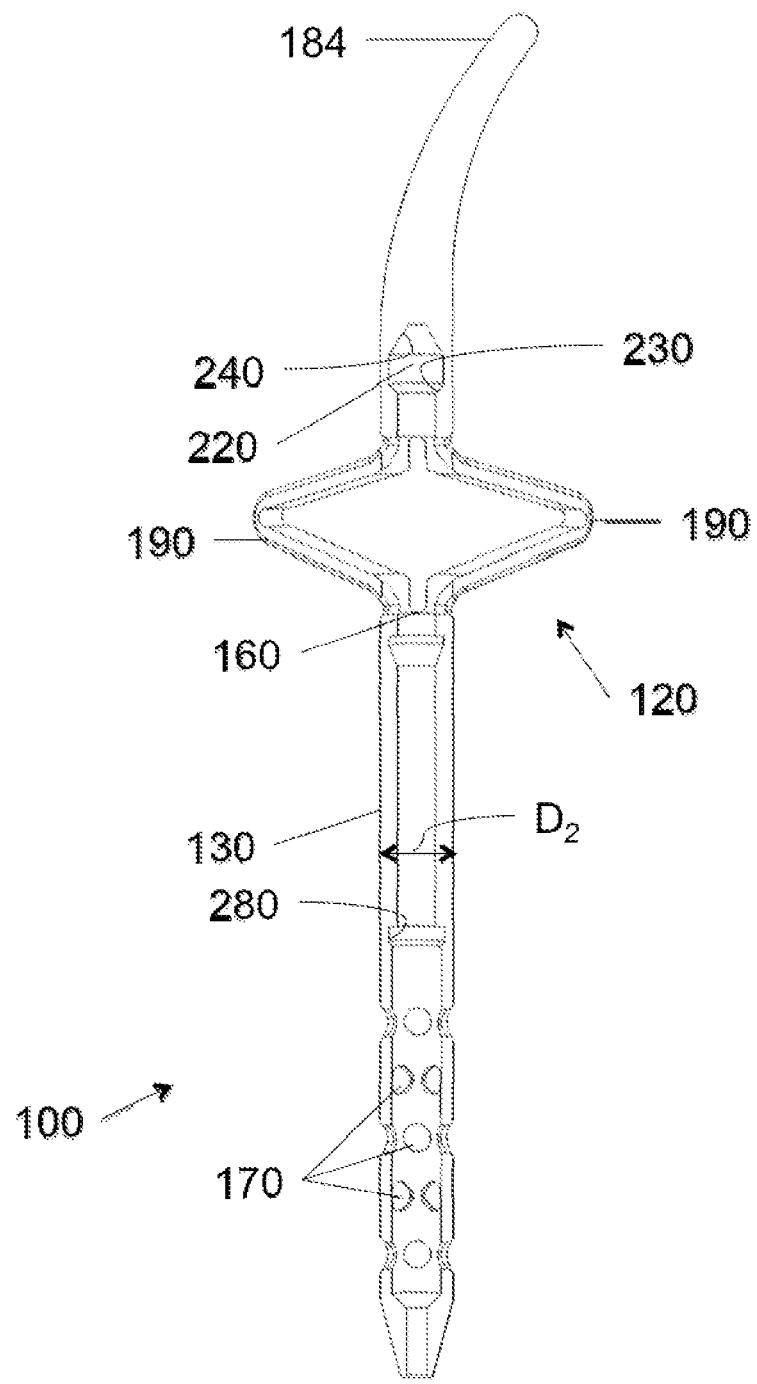
FIG. 8 is an enlarged partial sectional view of the urinary catheter of FIG. 1, with the core lumen removed.

The bladder retention mechanism 120 can be moved from the release position to the retention position by moving the core lumen 110 in a direction from the inlet end 140 toward the outlet end 150. Referring to FIGS. 7 and 8, the illustrated plug 210 has a first side 290 and a second side 300, the first side 290 being closer to the first inner surface 230 than the second side 300. The projection 250 defines an abutment stop 310 opposite the tip portion 260, having an opening 320 formed therein for receiving the plug 210. The plug 210 and abutment stop 310 are so dimensioned as to give a substantially bulbous appearance when the first side 290 of the plug 210 is inserted into the opening 320. As the bladder retention mechanism 120 is moved to the retention position, the abutment stop 310 comes in contact with first inner surface 130, thereby increasing friction against further movement (e.g., against the legs 190 of the bladder retention mechanism 120 collapsing). When the bladder retention mechanism 120 is fully moved to the retention position, the abutment stop 310 engages the first inner surface 130 and securely holds the legs 190 of the bladder retention mechanism 120 in a fixed, desired orientation relative to the longitudinal axis 200.

In some embodiments, once the bladder retention mechanism 120 is moved to the retention position, the bladder retention mechanism 120 can remain in that position substantially without requiring further user intervention or actuation. Once in the retention position, the tip portion 260 of the projection 250 engages the reduced-diameter portion 280 of the stent 130 to keep the bladder retention mechanism 120 in place. Therefore, the bladder retention mechanism 120 will remain in the retention position even if the core lumen 110 is subsequently disconnected therefrom.

The illustrated body portion 270 of the projection 250 has a cross section that is shaped and dimensioned to be retained in the stent 130 by friction, e.g., by an interference fit in one direction, while creating a slight gap or offset 330 in another direction (e.g., substantially perpendicular to the direction associated with the interference fit). In the illustrated embodiment, the body portion 270 of the projection 250 has a generally circular cross-sectional shape with one or more cutouts or recesses extending parallel to the longitudinal axis 200 so that the body portion 270 roughly resembles a paddle. In use, fluid enters the gap 330 at the stent inlet 160 toward a first direction 334. The fluid then flows in a direction parallel to the longitudinal axis 200 toward a second direction 336 (i.e., downwardly in FIG. 7). Subsequently, the fluid exits the stent 130 through the stent outlet 170 toward a third direction 338. In this regard, the fluid flows substantially external to the body portion 270 of the projection 250.

Figure 9:
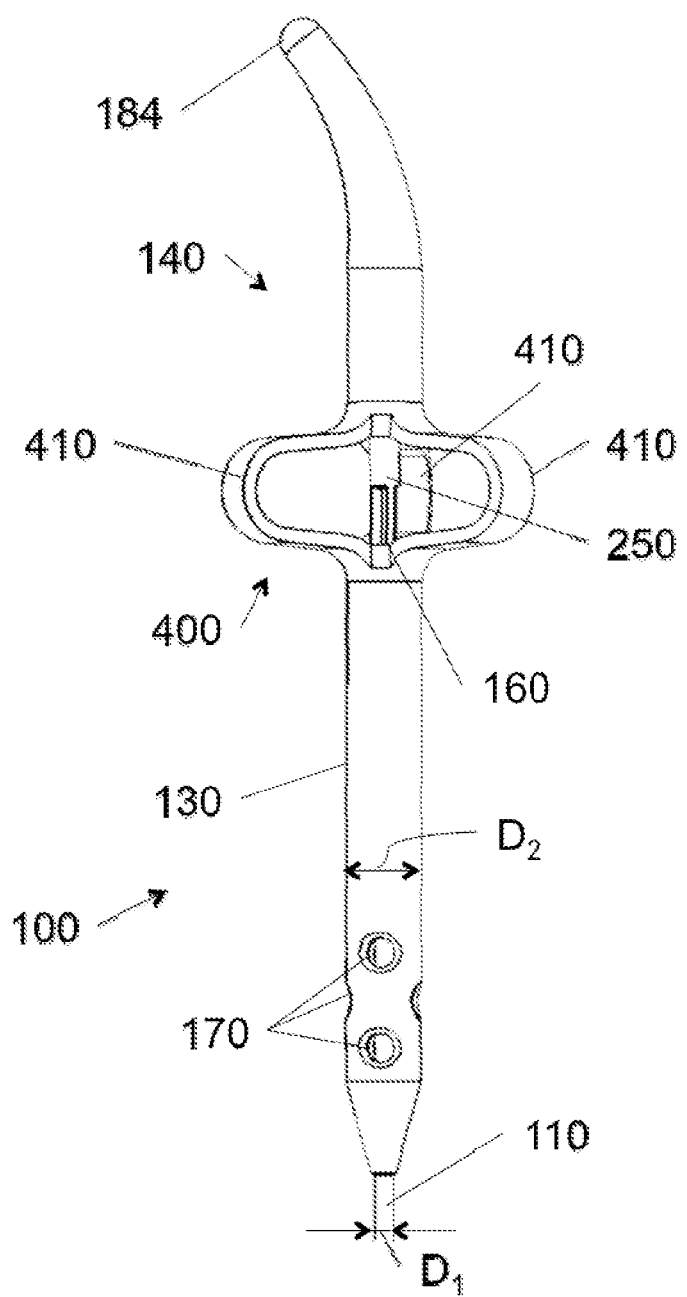
FIG. 9 is an enlarged partial perspective view of a bladder retention mechanism according to another embodiment of the invention.

FIG. 9 is an enlarged partial perspective view of a bladder retention mechanism 400 according to another embodiment of the invention. In this embodiment, the bladder retention mechanism 400 uses a Malecot type locking mechanism that includes a plurality of legs or wings 410 that are not necessarily linear. The illustrated legs 410 are joined at rounded or radiused corners with a respective bending radius. The illustrated bladder retention mechanism 400 hingedly moves from the release position to the retention position by bending the legs 410 about an axis extending substantially perpendicular to the longitudinal axis 200 or by otherwise reducing the bending radius. As explained below, for removal of the urinary catheter 100 from the urethra U, the bladder retention mechanism 400 hingedly moves from the retention position to the release position, by increasing the bending radius or by otherwise increasing the bending radius.

Figure 10:
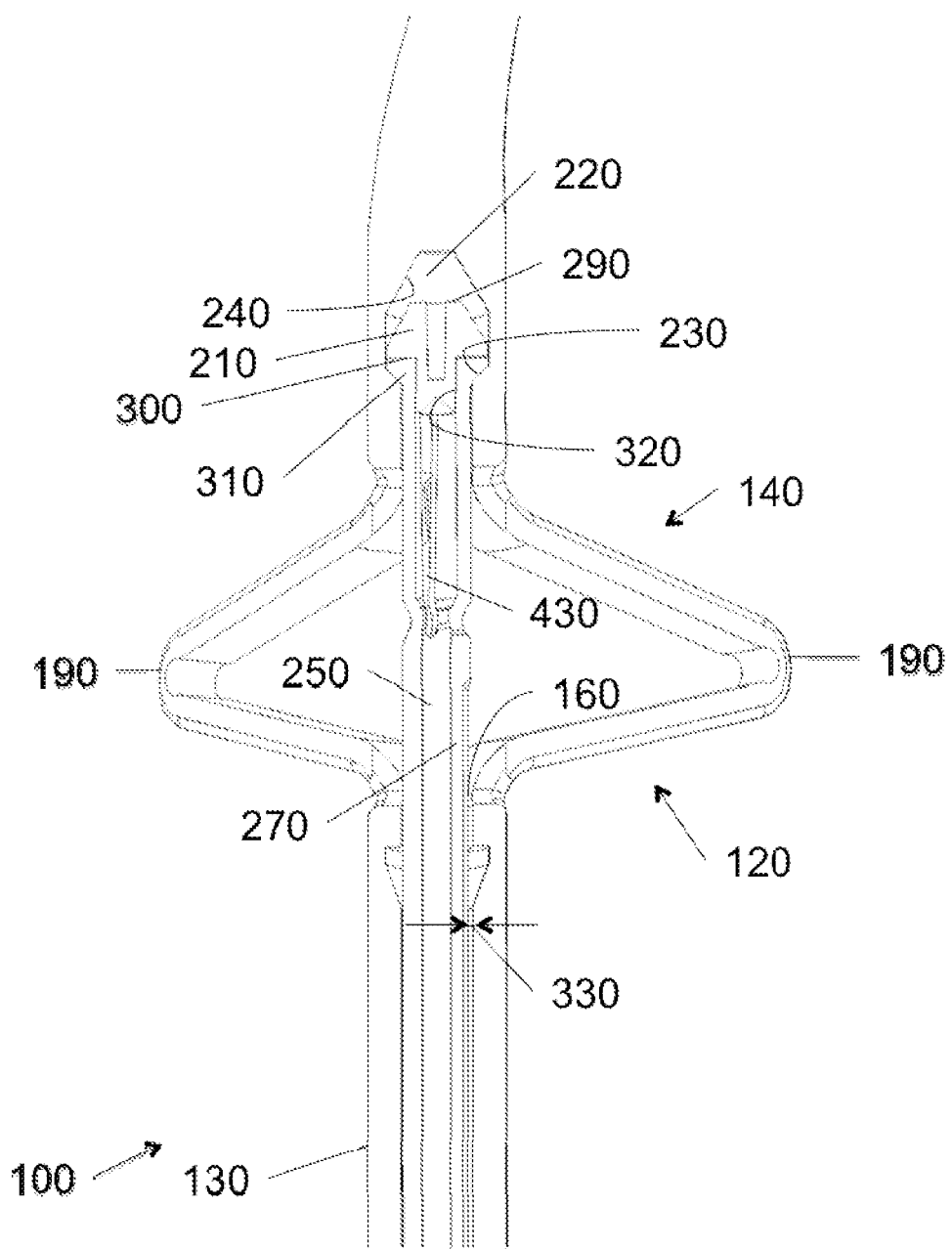
FIG. 10 is an enlarged partial cutaway view of the bladder retention mechanism of FIG. 1.

Referring also to FIG. 10, the illustrated abutment stop 310 of the projection 250 is configured to be removed or released from the plug 210 when a predetermined force is applied on the core lumen 110 in a direction from the inlet end 140 toward the outlet end 150. The plug 210 therefore stays in the socket 220, while the abutment stop 310 of the projection 250 is allowed to be pulled out toward the outlet end 150. The bladder retention mechanism 120 can thus return to a substantially straight configuration (e.g., by way of the resilience of the material) and be released from the bladder B and subsequently from the urethra, if the patient accidentally or intentionally applies an excessive force by pulling on the core lumen 110, thereby preventing damage to the bladder B and/or the urethra U.

Figure 11:
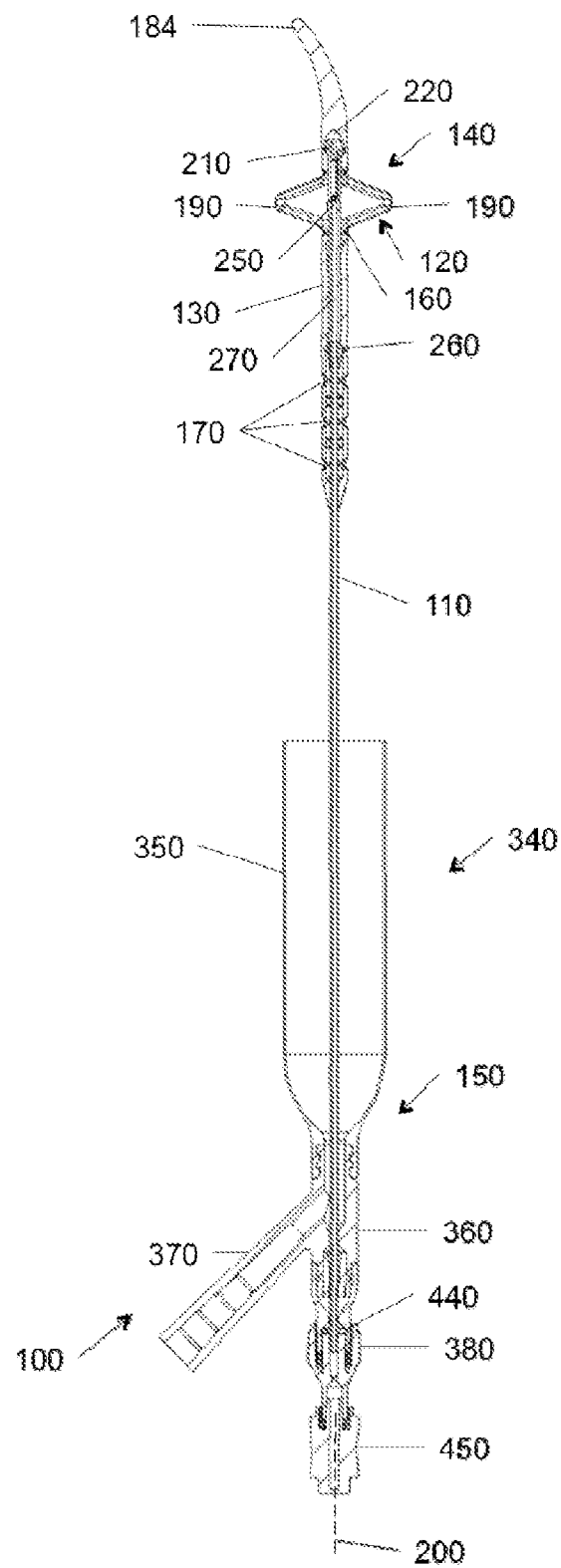
FIG. 11 is an enlarged sectional view of the outlet sheath of FIG. 1, including a condom component coupled to a pair of conduits.
Figure 12:
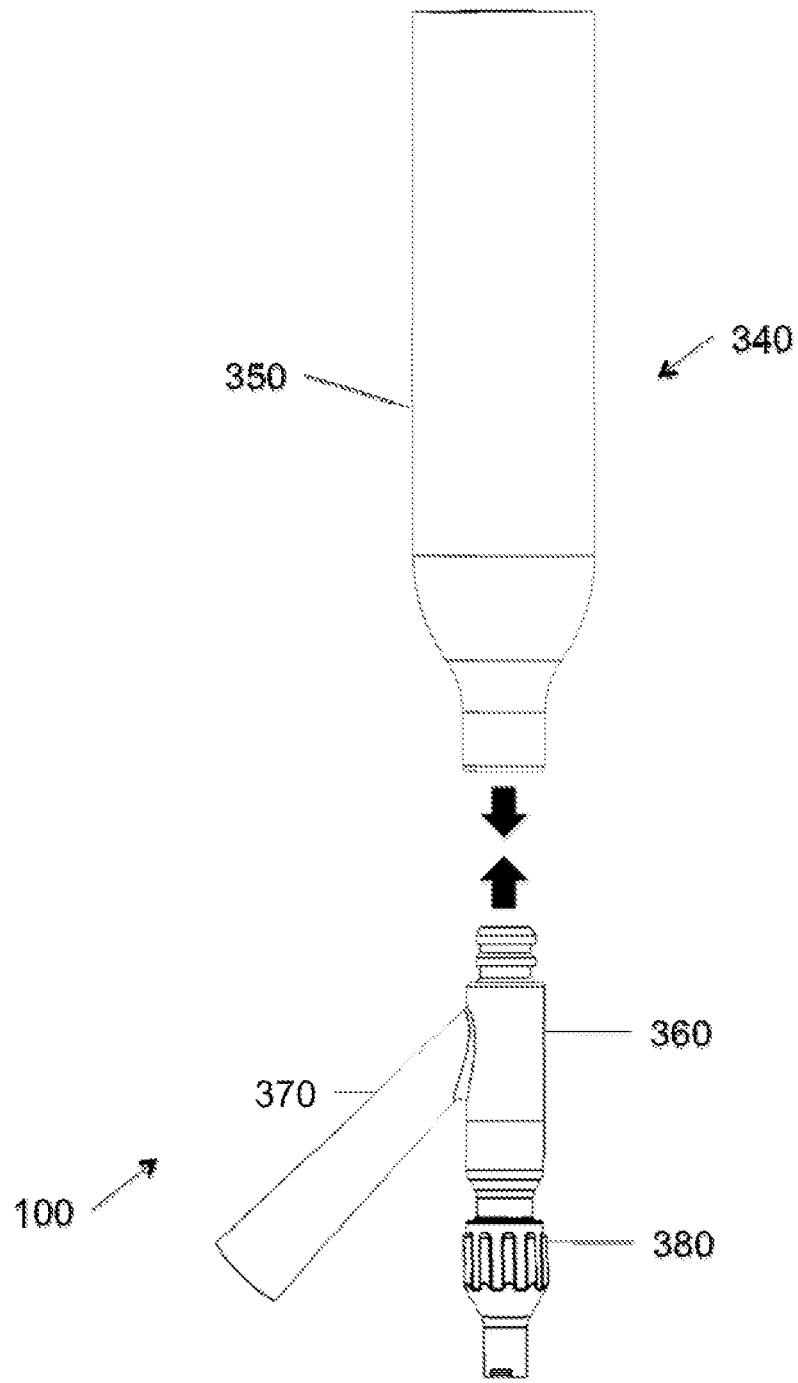
FIG. 12 is a side view of the outlet sheath of FIG. 1, illustrating the condom component removed from the pair of conduits.

Referring also to FIGS. 11 and 12, in the illustrated embodiment, an outlet sheath 340 is coupled to the outlet end 150 of the core lumen 110. The illustrated outlet sheath 340 is configured to receive fluid flowing from the stent outlet 170. In the illustrated embodiment, the outlet sheath 340 includes a condom component 350 coupled to first and second conduits 360, 370 to discharge the fluid. In other embodiments, other structures performing the same function as the condom component 350 disclosed herein can be used instead. In particular, embodiments of the urinary catheter 100 may be adapted for use with a female anatomy (see, e.g., FIG. 2), which includes among other changes a female counterpart to the outlet sheath and condom component such as the illustrated cup or funnel 420.

In the illustrated embodiment, the first conduit 360 is coupled to a first detachable coupler 380 such as a Tuohy-Borst mechanism that can removably lock an external component (not shown) to the first conduit 360. In use, any additional length of the core lumen 110 extending out from the first detachable coupler 380 can be cut or trimmed off, so that an end portion of the core lumen 110 is substantially flush with an end portion of the first detachable coupler 380. The first conduit 360 can be connected via the detachable coupler 380 to a reservoir of a saline solution, an antimicrobial or antibacterial solution, or medication, to flush the urethra U therewith, thereby inhibiting biofilm formation. Referring also to FIGS. 7, and 10, the illustrated projection 250 includes a slit or channel 430 formed therein adjacent the stent inlet 160. In some embodiments, the slit 430 is configured to open upon an internal pressure for example applied by the antimicrobial solution. In further embodiments, the slit 430 is configured to resiliently close in absence of the internal pressure. Once the slit 430 is closed, the fluid in the bladder B may present a force that tend to open the slit 430. However, the slit 430 may be configured to withstand this opening force by way of the resilience of the material surrounding the slit 430. Thus, once the slit 430 is closed, the flow or leakage of the fluid through the slit 430 may be substantially prevented despite the pressure of the fluid in the bladder B. In this regard, the slit 430 can act as a valve. In other embodiments, the slit 430 may stay open at all times; however, the surface tension of the fluid in the bladder B may operate to effectively seal or block the slit 430 in absence of the internal pressure. In still other embodiments, the slit 430 may be configured to allow for fluid to flow from the bladder B through the core lumen 110 when a negative pressure is applied therein, for example by a syringe to sample urine from the bladder B.

The detachable coupler 380 can allow for changing the outlet sheath 340 and/or external components, depending on the usage requirements or preferences for the particular urinary catheter 100. The coupler 380 has an O-ring 440 that is squeezed inwardly and tightened around the core lumen 110 when the first conduit 360 and the first detachable coupler 380 are coupled together. A second detachable coupler 450 distal to the first detachable coupler 380 could also be a Tuohy-Borst coupler or a Luer-Lock for attaching a syringe (not shown). For example, a syringe can be attached to the second detachable coupler 450 for instilling a saline or antimicrobial solution or drug through the core lumen 110 and out the slit 430 to the bladder B and urethra U. Moreover, when attached to the second detachable coupler 450, the syringe can withdraw or sample a desired volume of urine the bladder B to examine a bacterial load.

The second conduit 370 branches from the first conduit 360 for removably coupling to a reservoir or collection container (not shown). For example, the second conduit 370 can be attached to a collection container on the patient's leg or bedside. In the illustrated embodiment, the first and second conduits 360, 370 define an acute angle. In other embodiments, the second conduit 370 can extend at a non-zero angle relative to the first conduit 360.

In some embodiments, the outlet sheath 340 is coupled to a bellows or accordion adaptor (not shown) to adjust a distance from the bladder retention mechanism 120 to the outlet end 150 of the core lumen 110. Therefore, the outlet sheath 340 is allowed to be adjusted for different urethral lengths. In some embodiments, the bellows or accordion adaptor can be omitted.

Figure 13:
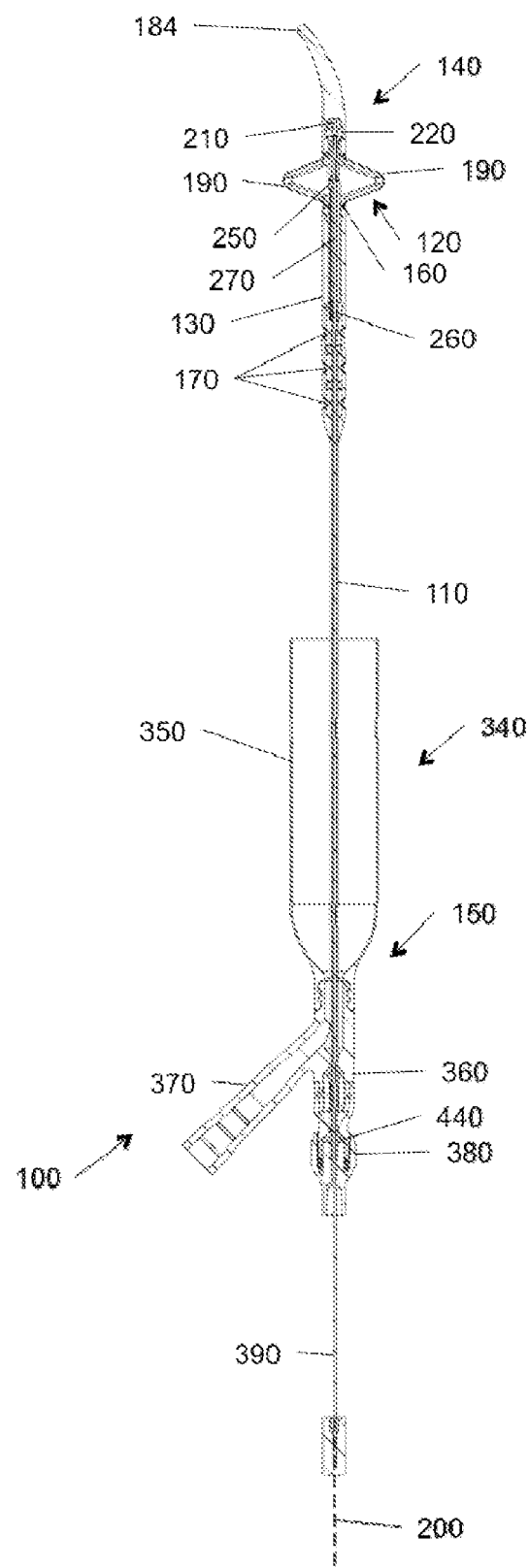
FIG. 13 is a sectional view of the urinary catheter of FIG. 1, illustrating a wire being inserted into a first conduit.

Referring to FIG. 13, to remove the urinary catheter 100 from the urethra U, a wire 390 can be inserted through the core lumen 110. The wire 390 is moved or threaded toward the inlet end 140 (i.e., upwardly in FIG. 13) until it comes in contact with the plug 210. Once the wire 390 is in contact with the plug 210, the plug 210 can be pushed toward the second inner surface 240, whereupon the plug 210 separates from the abutment stop 310. As the plug 210 continues to be pushed away from the abutment stop 310 against the second inner surface 240, the plug 120 is released or removed from the abutment stop 310, thereby allowing the abutment stop 310 to be released from the socket 220. The bladder retention mechanism 120 then hingedly returns to the substantially straightened release position. Once the bladder retention mechanism 120 is returned to the release position, the urinary catheter 100 can be safely pulled through the urethra U.

Figure 14:
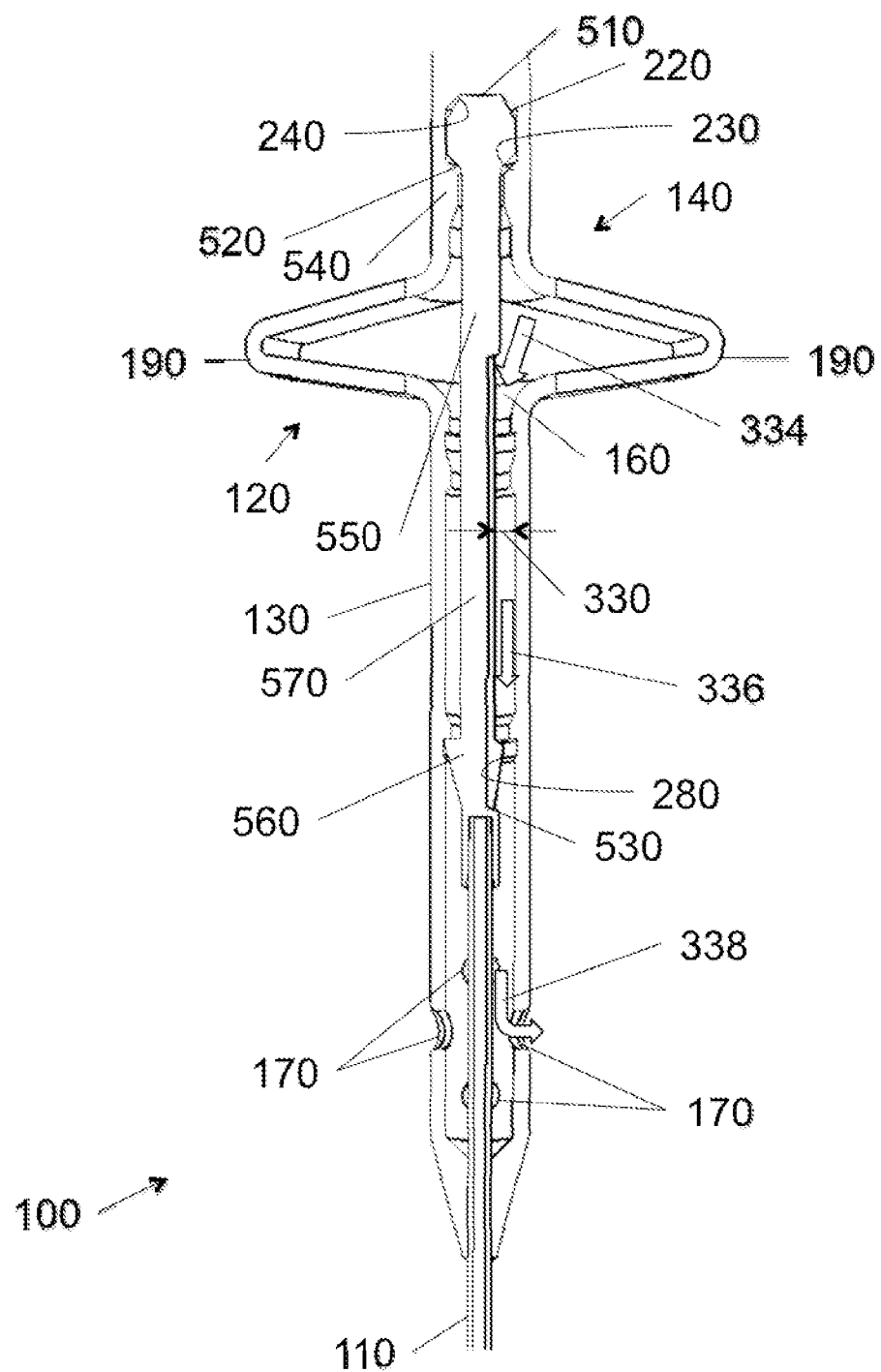
FIG. 14 is a cross-sectional view of the core lumen, bladder retention mechanism, and stent according to an embodiment of a urinary catheter.

FIGS. 14-19 show additional embodiments of the urinary catheter 100 in which numerical references are used as above unless otherwise indicated. In the embodiment of FIG. 14, a plug 510 fits into the socket 220, abutting the second inner surface 240, to maintain the bladder retention mechanism 120 in the retention position, as discussed above. The plug 510 includes a projection 550 which extends away from the plug 510 towards the outlet end 150 of the core lumen 110 (e.g. downwardly in FIG. 14). The surface joining the plug 510 to the projection 550 may include a tapered or curved surface 520 which abuts the first inner surface 230 of the bladder retention mechanism 120.

The projection 550 includes a tip or head portion 560 which has a larger cross section relative to an adjacent body portion 570. The tip portion 560 of the projection 550 resembles an arrowhead in cross section, as described above. In this embodiment the core lumen 110 is attached to a distal end of the tip portion 560 (e.g. by suitable adhesive and/or friction fit) such that a pulling force exerted on the core lumen 110 is transferred to the plug 510 via the projection 550.

In the embodiment of FIG. 14, the plug 510 is retained by a neck 540 of the bladder retention mechanism 120. When a suitable pulling force is applied to the core lumen 110, the plug 510 is pulled and squeezes through the neck 540, thereby placing the bladder retention mechanism 120 in the release position. As discussed above, being in the release position permits the legs 190 to straighten towards the longitudinal axis 200, allowing the catheter 100 to be removed from the bladder. In some embodiments, the plug 510 is relatively rigid and the neck 540 is resilient so that when the pulling force is applied the neck 540 stretches to allow the plug 510 to move through. In other embodiments, the plug 510 is relatively resilient and the neck 540 is relatively rigid so that when the pulling force is applied the plug 510 deforms to move through the neck 540. In still other embodiments, the plug 510 and the neck 540 each have varying levels of resilience through which each deforms to a sufficient degree to permit the plug 510 to move through the neck 540 when a pulling force is applied. Furthermore, the properties of the plug 510 and neck 540 are such that the plug 510 is retained in the neck 540 during normal use.

Figure 15:
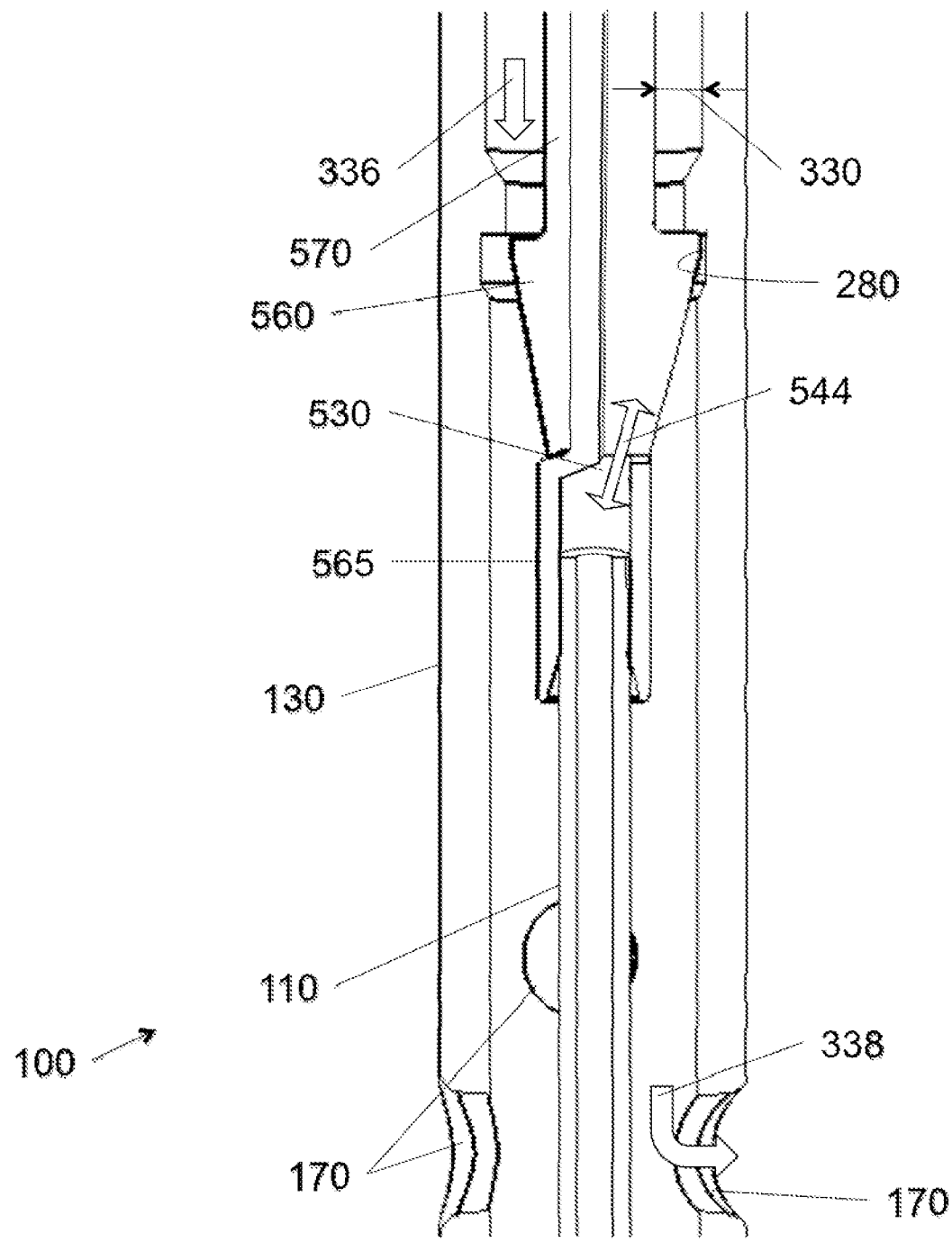
FIG. 15 is a cross-sectional view of a portion of the urinary catheter of FIG. 14.
Figure 16:
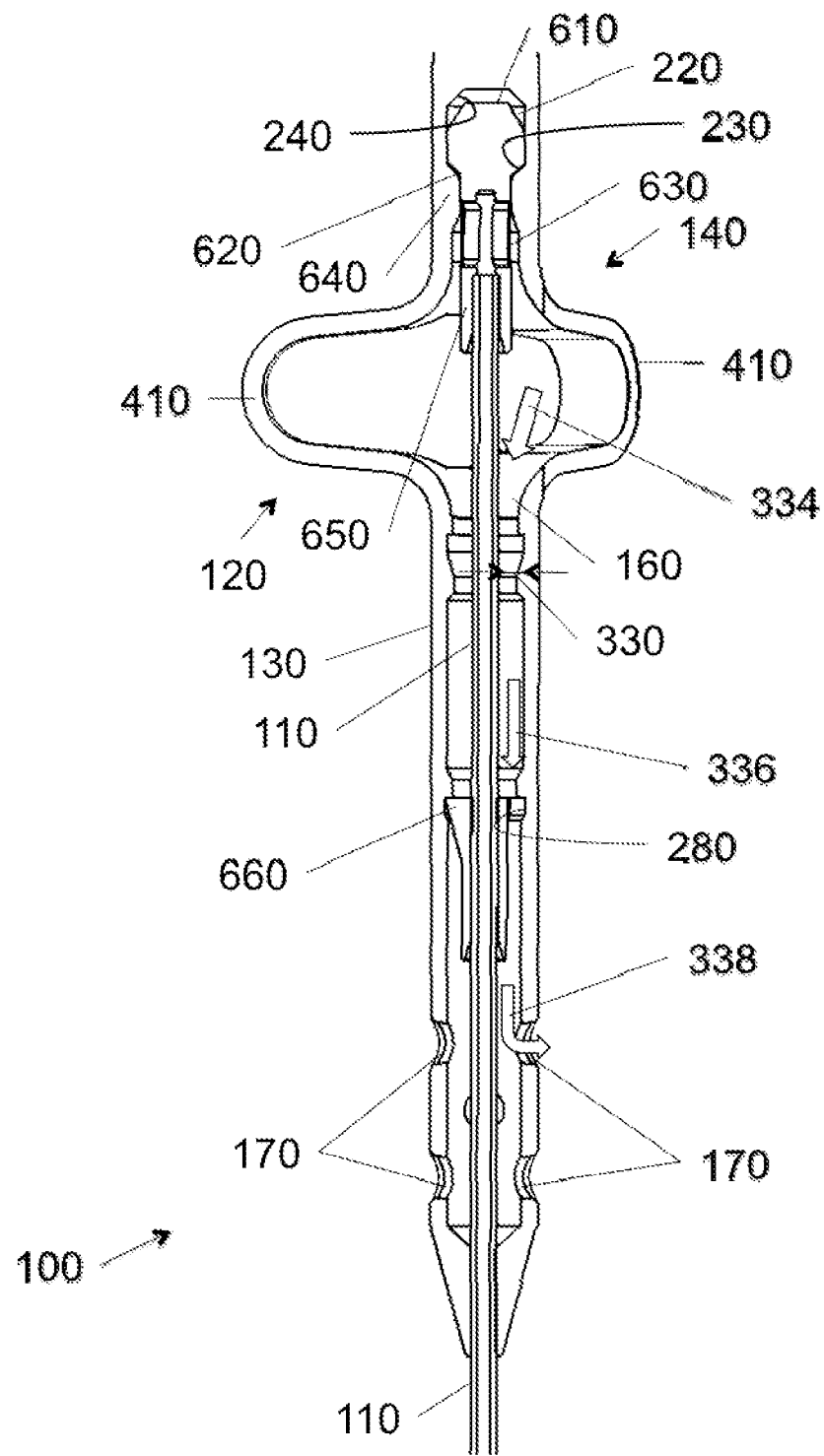
FIG. 16 is a cross-sectional view of the core lumen, bladder retention mechanism, and stent according to an embodiment of a urinary catheter.

FIGS. 14 and 15 show an embodiment of the urinary catheter 100 in which urine may be sampled from the bladder B or urethra U or a material (e.g. antimicrobial solution or drug) may be introduced into the bladder B or urethra U at a location near the tip portion 560 of the extension 550 of the plug 510. FIG. 15 shows a cross-section of the region where the end of the core lumen 110 is joined to the tip portion 560. As shown in FIG. 15, the tip portion 560 is joined to the core lumen 110 by a cylindrical extension 565 which terminates in an opening 530 through which fluid can flow 544 in either direction. Thus, fluid may be introduced or sampled through opening 530 by application of positive or negative pressure through the core lumen 110.

FIGS. 16, 17A, 17B, and 17C show cross-sectional views of another embodiment of the urinary catheter 100. A plug 610 fits into the socket 220, abutting the second inner surface 240, to maintain the bladder retention mechanism 120 in the retention position, as discussed above. The plug 610 includes a projection 650 which extends away from the plug 610 towards the outlet end 150 of the core lumen 110 (e.g. downwardly in FIG. 16). The surface joining the plug 610 to the projection 650 may include a tapered or curved surface 620 which abuts the first inner surface 230 of the bladder retention mechanism 120. The plug 610 is retained by a neck 640 of the bladder retention mechanism 120. As discussed above with regard to FIG. 14, the plug 610 and neck 640 each have a level of rigidity and/or resilience which permits the plug 610 to be pulled through the neck 640 when a sufficient pulling force is applied to the projection 650. The projection 650 terminates in a hollow cylindrical opening into which the core lumen 110 is inserted and attached (e.g. using suitable adhesive and/or friction fit), such that a pulling force that is applied to the core lumen 110 is transferred to the projection 650 and in turn to the plug 610. Unlike the embodiment shown in FIG. 15, in the embodiment of FIG. 16 the tip portion 660 is not an extension of the projection 650 and instead is a separate element that is attached (e.g. with adhesive and/or friction fitting) to the core lumen 110.

Figure 17A:
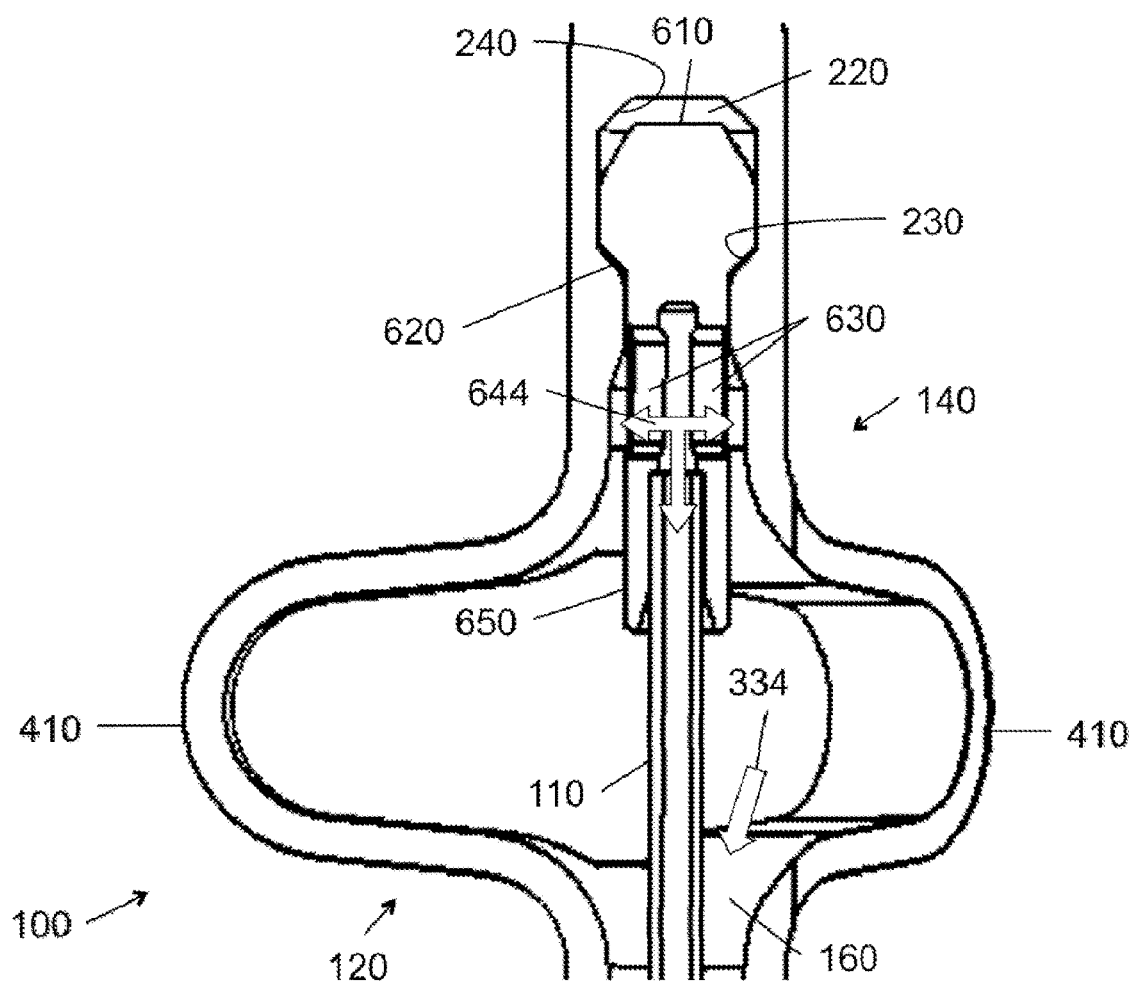
FIGS. 17A, 17B, and 17C are cross-sectional views of a portion of the urinary catheter of FIG. 16.
Figure 17B:
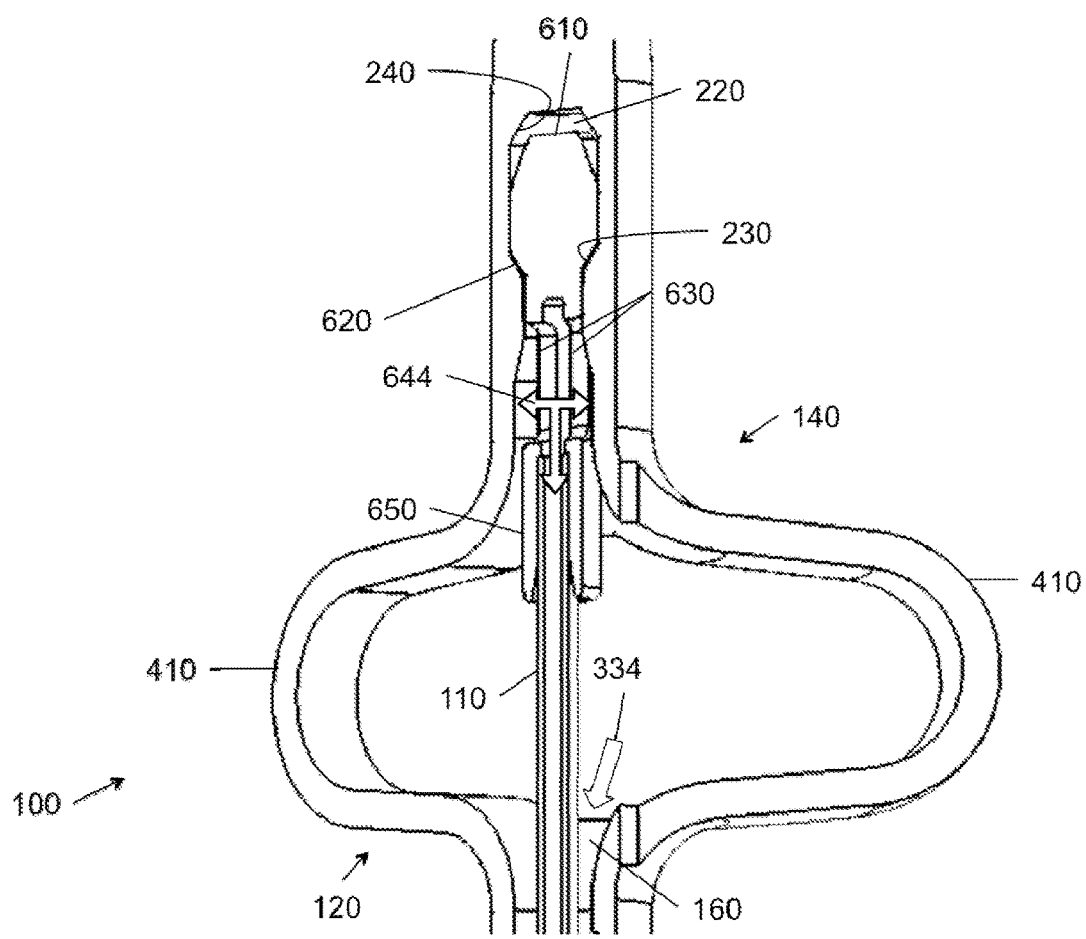
Figure 17C:
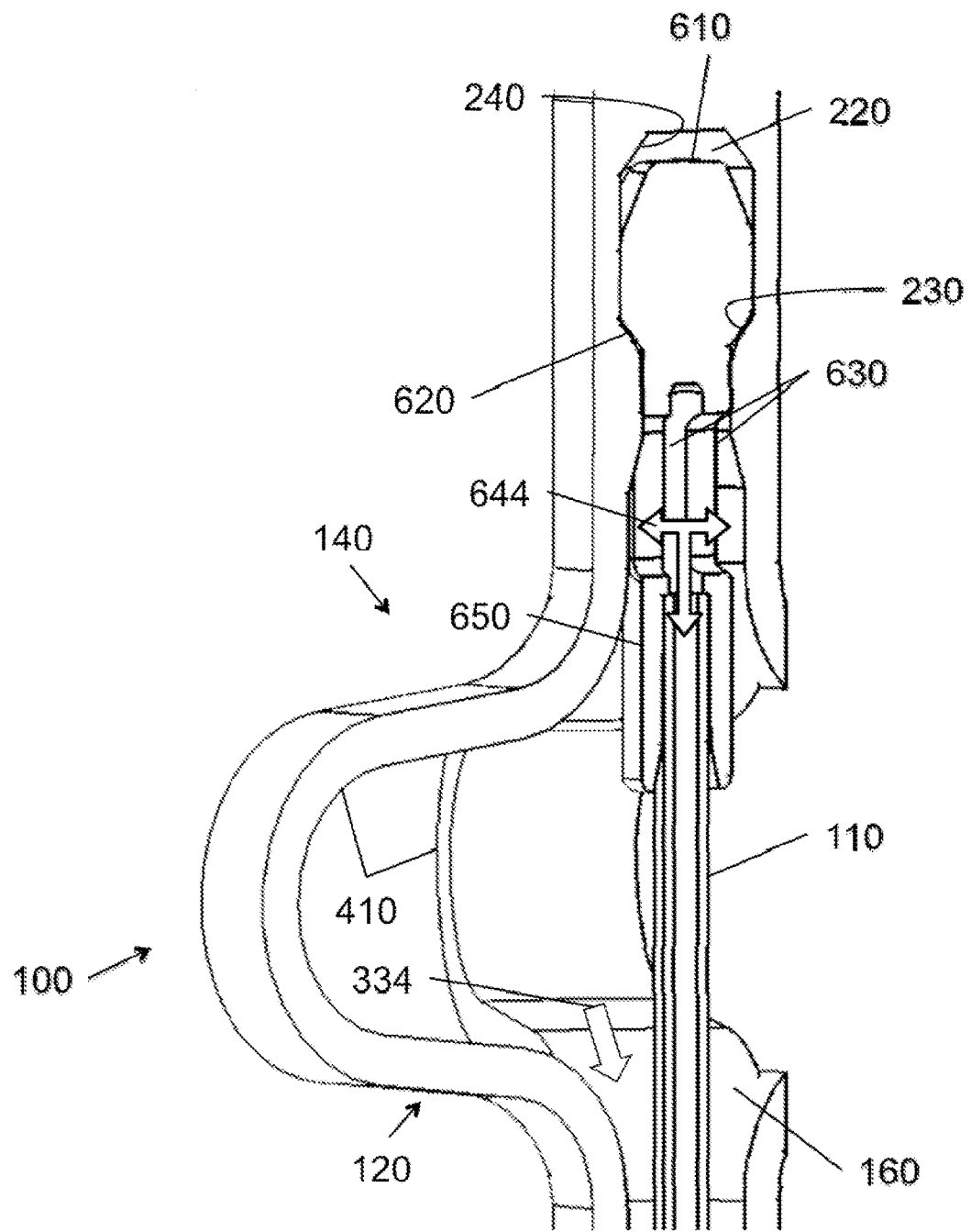

The embodiment of FIGS. 16, 17A, 17B, and 17C show an embodiment of the urinary catheter 100 in which urine may be sampled from the bladder B or a material (e.g. antimicrobial solution or drug) may be introduced into the bladder B at a location adjacent to the neck 640 of the bladder retention mechanism 120. FIGS. 17A, 17B, and 17C show cross-sectional views of the region where the end of the core lumen 110 is joined to the projection 650. The core lumen 110 is aligned with a portion of the projection 650 which includes a fluid channel and one or more lateral openings 630 which permit fluid to flow 644 between the core lumen 110 and the bladder B. The one or more lateral openings 630 open to a space below the neck 640 (as seen in FIGS. 16, 17A, 17B, and 17C) in which there is a gap between the projection 650 and the bladder retention mechanism 120. Thus, fluid may be introduced or sampled through the one or more openings 630 by application of positive or negative pressure through the core lumen 110.

Figure 18:
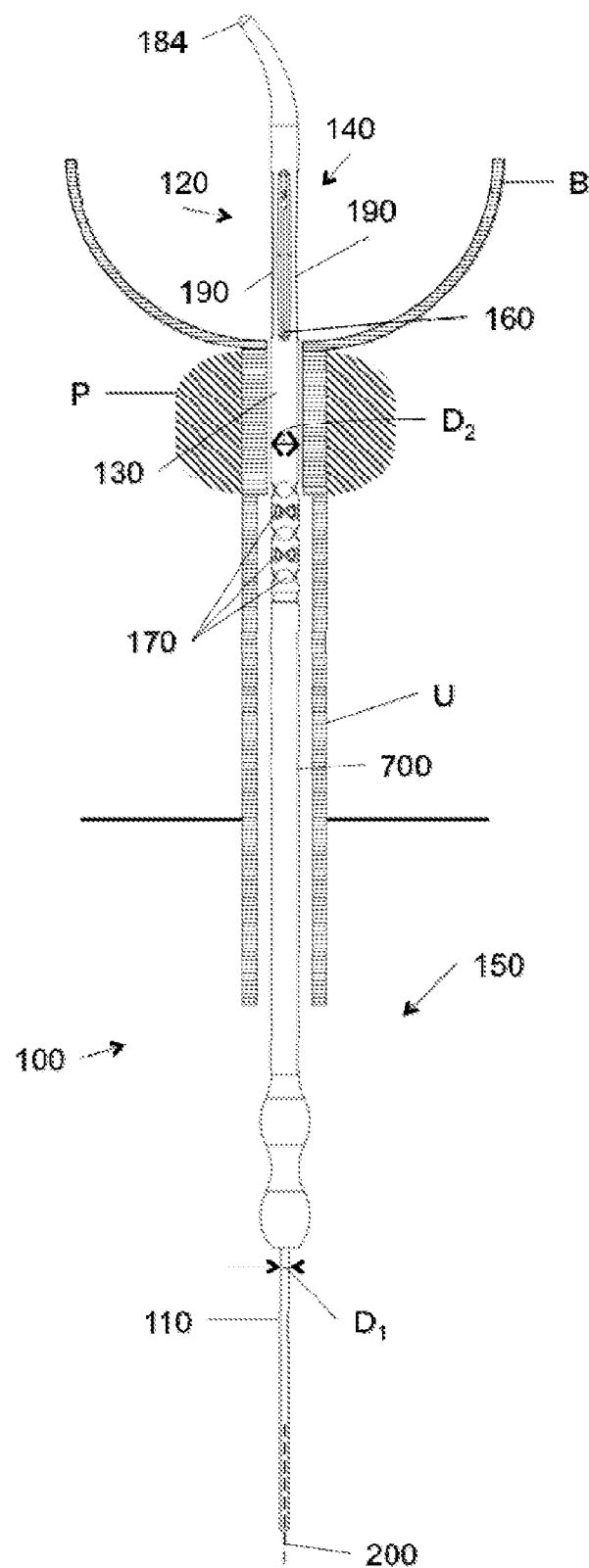
FIG. 18 shows a urinary catheter prior to removal from a patient's bladder.
Figure 19:
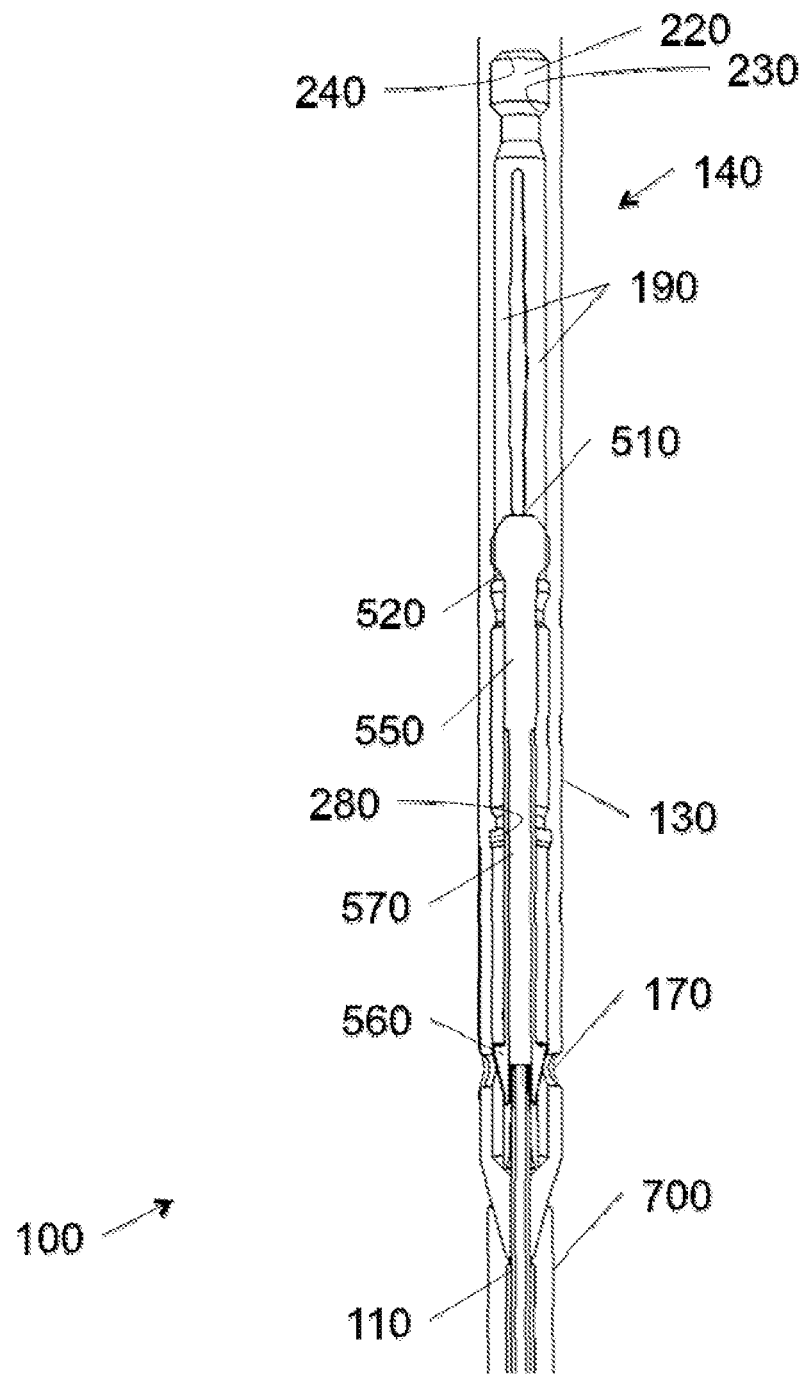
FIG. 19 shows a cross-sectional view of a urinary catheter with its bladder retention mechanism in a release position.

FIGS. 18 and 19 show steps involved in removal of the urinary catheter from a patient's bladder. After external components other than the core lumen 110 have been removed, a stent sheath 700 is slid over the core lumen until it abuts the end of the stent 130. In various embodiments, the stent sheath 700 is configured to have a contacting surface that is complementary to that of the end of the stent 130. Holding the stent 130 steady using the stent sheath 700, a pulling force is applied to the core lumen 110, which in turn pulls the plug 510/610 through the neck 540/640. Once the plug 510/610 has been pulled clear of the neck 540/640, the legs 190/400 of the bladder retention mechanism 120 retract towards one another so that the bladder retention mechanism 120 assumes a narrower profile suitable for removal from the bladder B.

Element 280 of the stent 130 is referred to herein as a "reduced-diameter portion 280" simply for convenience; those of skill in the art will understand that, in view of the tapered nature of this portion, some regions of element 280 may also have an increased diameter, depending on which features of the stent 130 element 280 is compared to. Furthermore, one skilled in the art will also understand that, when the bladder retention mechanism 120 is in the release position, the tip portion 260/560/660 rests on the reduced-diameter portion 280, and is prevented from further moving toward either the outlet end 150 or the inlet end 140 of the core lumen 110.

Thus, the invention provides, among other things, a urinary catheter including a core lumen, a bladder retention mechanism, and a stent, wherein the bladder retention mechanism hingedly moves between a release position and a retention position, and wherein the stent is configured to discharge fluid around the core lumen and into the urethra. Various features and advantages of the invention are set forth in the following claims.

What is claimed is:

1. A urinary catheter comprising:
a core lumen insertable into a urethra, the core lumen defining an inlet end having a single inlet and an outlet end opposite the inlet end;
a bladder retention mechanism coupled to the inlet end of the core lumen for hingedly moving between a release position and a retention position;
a stent coaxially mounted on the core lumen adjacent the bladder retention mechanism, the stent defining a stent inlet in fluid communication with the single inlet of the core lumen and configured to transport a fluid from a bladder,
and a stent outlet configured to discharge the fluid around an external surface of the core lumen and into contact with the urethra;
wherein the core lumen defines a first outermost diameter, wherein the stent defines a second outermost diameter, and wherein the second outermost diameter is greater than the first outermost diameter;
wherein the stent tapers at its bottom from the second outermost diameter towards the first outermost diameter.

2. The urinary catheter of claim 1, further comprising an outlet sheath coupled to the outlet end of the core lumen, wherein the outlet sheath is configured to receive the fluid, and wherein the outlet sheath includes at least one conduit to discharge the fluid.

3. The urinary catheter of claim 2, wherein the outlet sheath includes a first conduit and a second conduit branching from the first conduit for removably coupling to a reservoir.

4. The urinary catheter of claim 3, wherein the first and second conduits define an acute angle.

5. The urinary catheter of claim 2, wherein the outlet sheath is coupled to a bellows to adjust a distance from the bladder retention mechanism to the outlet end of the core lumen.

6. The urinary catheter of claim 1, wherein the core lumen defines a longitudinal axis, and wherein the bladder retention mechanism includes a leg extending substantially parallel to the longitudinal axis when the bladder retention mechanism is in the release position.

7. The urinary catheter of claim 1, wherein the inlet end of the core lumen is coupled to a plug, wherein the bladder retention mechanism includes a socket formed therein, the socket having first and second inner surfaces, the first inner surface being closer to the outlet end of the core lumen than the second inner surface, wherein the plug is insertable into the socket, and wherein the plug abuts the second inner surface when the bladder retention mechanism is in the release position.

8. The urinary catheter of claim 7, wherein a projection extends from the plug toward the outlet end of the core lumen, wherein the stent defines a reduced-diameter portion, and wherein the projection is matingly receivable into the reduced-diameter portion.

9. The urinary catheter of claim 1, wherein the core lumen defines a longitudinal axis, and wherein the bladder retention mechanism includes a leg extending from the longitudinal axis when the bladder retention mechanism is in the retention position.

10. The urinary catheter of claim 1, wherein the bladder retention mechanism includes a socket formed therein, the socket having first and second inner surfaces, the first inner surface being closer to the outlet end than the second inner surface, wherein the inlet end of the core lumen defines an abutment stop, and wherein the abutment stop engages the first inner surface when the bladder retention mechanism is in the retention position.

11. The urinary catheter of claim 10, wherein the bladder retention mechanism includes a leg having a retention area in contact with the bladder, and wherein moving the abutment stop toward the first inner surface increases the retention area.

12. The urinary catheter of claim 10, wherein the inlet end of the core lumen is coupled to a plug, and wherein the inlet end of the core lumen is configured to be released from the plug when a predetermined force is applied on the core lumen in a direction from the inlet end toward the outlet end.

13. The urinary catheter of claim 1, wherein the stent sheath is dimensioned to matingly receive the stent.

14. A method for catheterization, the method comprising:
advancing a core lumen through a urethra of a patient into a bladder, wherein the core lumen defines an inlet end having a single inlet and an outlet end opposite the inlet end, wherein a bladder retention mechanism is coupled to the inlet end in a release position, wherein a stent is coaxially mounted on the core lumen adjacent the bladder retention mechanism, and wherein the stent defines a stent inlet in fluid communication with the single inlet of the core lumen and configured to receive a fluid from the bladder, and a stent outlet configured to discharge the fluid around an external surface of the core lumen and into contact with the urethra; and
moving the core lumen in a direction from the inlet end toward the outlet end,
whereupon the bladder retention mechanism hingedly moves from the release position to a retention position;
wherein the core lumen defines a first outermost diameter, wherein the stent defines a second outermost diameter, and wherein the second outermost diameter is greater than the first outermost diameter;
wherein the stent tapers at its bottom from the second outermost diameter towards the first outermost diameter.

15. The method of claim 14, further comprising coupling an outlet sheath to the outlet end, wherein the outlet sheath is configured to receive the fluid, and wherein the outlet sheath includes at least one conduit to discharge the fluid.

16. The method of claim 14, wherein the outlet sheath includes a first conduit and a second conduit branching from the first conduit, wherein the method further comprises removably coupling a reservoir of fluid to the first conduit, and injecting the fluid into the first conduit.

17. The method of claim 14, wherein the core lumen defines a longitudinal axis, wherein the bladder retention mechanism includes a leg, and wherein moving the core lumen in a direction from the inlet end toward the outlet end moves the leg from a position substantially parallel to the longitudinal axis to a position extending away from the longitudinal axis.

18. The method of claim 14, wherein the bladder retention mechanism includes a leg having a retention area in contact with the bladder, and wherein moving the core lumen in a direction from the inlet end toward the outlet end increases the retention area.

19. The method of claim 14, wherein a stent sheath is slidably coupled to the stent, and wherein the stent sheath is slidably removed from the stent when the bladder retention mechanism is in the retention position.

20. The method of claim 14, wherein the inlet end of the core lumen is coupled to a plug, wherein the bladder retention mechanism includes a socket formed therein, the socket having first and second inner surfaces, the first inner surface being closer to the outlet end than the second inner surface, wherein the plug is insertable into the socket, and wherein the plug is positioned closer to the second inner surface than the first inner surface when the bladder retention mechanism is in the retention position, and wherein the method further comprises inserting a wire through the core lumen when the bladder retention mechanism is in the retention position, and moving the plug to a position abutting the second inner surface, whereupon the bladder retention mechanism returns to the release position.

21. A urinary catheter comprising:
 a core lumen insertable into a urethra, the core lumen defining an inlet end having a single inlet and an outlet end opposite the inlet end, the inlet end of the core lumen being attached to a plug;
 a bladder retention mechanism for hingedly moving between a release position and a retention position, the bladder retention mechanism having a socket formed therein into which the plug is fitted; and
 a stent coaxially mounted on the core lumen adjacent the bladder retention mechanism, the stent defining a stent inlet in fluid communication with the single inlet of the core lumen and configured to receive a fluid from a bladder, and a stent outlet configured to discharge the fluid around an external surface of the core lumen and into contact with the urethra,
 wherein a pulling force applied to the core lumen removes the plug from the socket such that the bladder retention mechanism is in the release position;
 wherein the core lumen defines a first outermost diameter, wherein the stent defines a second outermost diameter, and wherein the second outermost diameter is greater than the first outermost diameter;
 wherein the stent tapers at its bottom from the second outermost diameter towards the first outermost diameter.

22. The urinary catheter of claim 21, further comprising a fluid channel in fluid communication with the inlet end of the core lumen to provide one of fluid sampling and fluid injection to one of a bladder and a urethra.

23. The urinary catheter of claim 22, wherein the fluid channel is adjacent to one of the stent and the bladder retention mechanism.

\* \* \* \* \*